(12) United States Patent
Kannemeier et al.

(10) Patent No.: US 10,093,903 B2
(45) Date of Patent: Oct. 9, 2018

(54) PRODUCTION OF VIRUS-RECEPTIVE PLURIPOTENT STEM CELL (PSC)-DERIVED HEPATOCYTES

(71) Applicant: FUJIFILM Cellular Dynamics, Inc., Madison, WI (US)

(72) Inventors: Christian Kannemeier, Madison, WI (US); Elisabeth Enghofer, Madison, WI (US); Lisa Harms, Madison, WI (US)

(73) Assignee: FUJIFILM Cellular Dynamics, Inc., Madison, WI (US)

( * ) Notice: Subject to any disclaimer, the term of this patent is extended or adjusted under 35 U.S.C. 154(b) by 0 days.

(21) Appl. No.: 15/297,420

(22) Filed: Oct. 19, 2016

(65) Prior Publication Data

US 2017/0107485 A1 Apr. 20, 2017

Related U.S. Application Data

(60) Provisional application No. 62/243,237, filed on Oct. 19, 2015.

(51) Int. Cl.
| | |
|---|---|
| *C12N 5/00* | (2006.01) |
| *C12N 5/074* | (2010.01) |
| *C12N 15/85* | (2006.01) |
| *C07H 21/04* | (2006.01) |
| *A01K 67/00* | (2006.01) |
| *C12N 5/071* | (2010.01) |
| *G01N 33/50* | (2006.01) |

(52) U.S. Cl.
CPC .......... *C12N 5/067* (2013.01); *G01N 33/5067* (2013.01); *C12N 2500/90* (2013.01); *C12N 2501/01* (2013.01); *C12N 2501/727* (2013.01); *C12N 2506/02* (2013.01); *C12N 2506/025* (2013.01); *C12N 2506/45* (2013.01); *G01N 2333/02* (2013.01)

(58) Field of Classification Search
CPC .. A61K 2300/00; A61K 35/407; C12N 5/067; C12N 2501/11; C12N 2501/155
See application file for complete search history.

(56) References Cited

U.S. PATENT DOCUMENTS

| 8,481,317 B2 | 7/2013 | Yu et al. |
| 2014/0242595 A1 | 8/2014 | Yu et al. |

FOREIGN PATENT DOCUMENTS

| CA | 2864301 | | 8/2013 |
| WO | WO 2003/011209 | | 2/2003 |
| WO | WO 2013/096457 | | 6/2013 |
| WO | WO2014124527 | * | 8/2014 |
| WO | WO 2015/164228 | | 10/2015 |

OTHER PUBLICATIONS

Shlomai et al. "Modeling host interactions with hepatitis B virus using primary and induced pluripotent stem cell-derived hepatocellular systems", PNAS, 2014, 111(33):12193-12198.*
Shlomai et al. "Modeling host interactions with hepatitis B virus using primary and induced pluripotent stem cell-derived hepatocellular systems", PNAS, 2014, 111(33): Supplemental:pdf pp. 1-9.*
Santa Cruz Biotechnology, Jak inhibitor 1, product sheet: pdf p. 1-6.*
Chen et al., "Rapid generation of mature hepatocyte-like cells from human induced pluripotent stem cells by an efficient three-step protocol," *Hepatology*, 55(44): 1193-1203, 2012.
Gripon et al., "Reproducible high level infection of cultured adult human hepatocytes by hepatitis B virus: effect of polyethylene glycol on adsorption and penetration," *Virology*, 192(2):534-540, 1993.
Ogawa et al.,"Three-dimensional culture and cAMP signaling promote the maturation of human pluripotent stem cell-drived hepatocytes," *Development*, 140(15):3285-3296, 2013.
PCT International Search Report and Written Opinion issued in International Application No. PCT/US2016/057598, dated Dec. 6, 2016.
Shlomai et al. ,"Modeling host interactions with hepatitis B virus using primaiy and induced pluripotent stem cell-derived hepatocellular systems," *Proceedings of the National Academy of Sciences of the United States of Arnerica*,111(33):12193-12198, 2014.

* cited by examiner

*Primary Examiner* — Barry A Chestnut
(74) *Attorney, Agent, or Firm* — Parker Highlander PLLC

(57) ABSTRACT

The present disclosure provides methods for maturing hepatocytes comprising culturing with cyclic adenosine monophosphate and a Janus kinase inhibitor. There is also provided a method for screening inhibitors of hepatitis B virus infection and/or replication.

24 Claims, 9 Drawing Sheets

PRODUCTION OF VIRUS-RECEPTIVE PLURIPOTENT STEM CELL (PSC)-DERIVED HEPATOCYTES

The present application claims the priority benefit of U.S. provisional application No. 62/243,237, filed Oct. 19, 2015, the entire contents of which are incorporated herein by reference.

BACKGROUND OF THE INVENTION

1. Field of the Invention

The present invention relates generally to the field of molecular biology, stem cells and differentiated cells. More particularly, it concerns maturation of pluripotent stem cell-derived hepatic lineage cells that are receptive to virus infection, particularly hepatitis B virus.

2. Description of Related Art

In vitro model systems based on hepatocytes have been used to better understand the role of hepatocytes in physiological processes of the liver and in studying diseases or conditions of the liver such as hepatitis B infection (HBV), cirrhosis, liver injury, and hepatocellular carcinoma. These model systems are also used for drug metabolism studies, screening of drugs such as anti-HBV drugs, and cell-based therapy for the treatment of liver diseases. While primary human hepatocytes have been commonly used in biological and biopharmaceutical research, they are in limited supply as they do not proliferate in culture. Moreover, primary human hepatocytes rapidly lose their hepatic phenotype shortly after isolation from the in vivo environment (Guillouzo et al., 1998), and the drug metabolic ability of human primary hepatocytes exhibits significant differences between donors. In addition, while primary human hepatocytes support HBV infection, the infection is not robust even with supplementation of cell-culture medium with dimethyl sulfoxide or polyethylene glycol (Gripon et al., 1988; Gripon et al., 1993).

The ability to direct the differentiation of human pluripotent stem cells (PSCs) such as induced pluripotent stem cells and embryonic stem cells to specific lineages including hepatocytes provides access to unlimited numbers of human hepatocytes for a wide range of applications that include development of new treatments for a spectrum of diseases, the establishment of platforms for drug discovery and predictive toxicology and the creation of in vitro models of disease. The availability of an unlimited supply of patient-specific functional hepatocytes would greatly facilitate both the drug development and the eventual clinical application of hepatocyte transplantation. Thus, there has been significant effort to develop PSC-derived hepatocytes that recapitulate the properties of in situ primary hepatocytes as an alternative, unlimited source of hepatocytes. In general, these methods induce differentiation of a monolayer of PSCs with the addition of pathway agonists and antagonists that are known to regulate endoderm induction and hepatic specification. For example, hepatocyte growth factor (HGF) was shown to synergize with activin A and Wnt3a for endodermal induction and subsequent culture in maturation media containing oncostatin M resulted in hepatocytes positive for albumin (Chen et al., 2012).

However, the currently known protocols for producing PSC-derived hepatocytes produce immature hepatocytes that do not display functional levels of key drug-metabolizing enzymes and do not efficiently replicate hepatitis B virus. Therefore, there is a need for methods to produce more mature PSC-derived hepatocytes for therapeutic and research use, especially hepatocytes capable of hepatitis B virus replication for use as models in screening for anti-HBV drugs.

SUMMARY OF THE INVENTION

The present disclosure provides methods of producing virus-receptive, particularly HBV-receptive, hepatocytes from pluripotent stem cell (PSC)-derived hepatocytes under specific hepatocyte maturation culture conditions. In a first embodiment, there is provided an in vitro method of producing virus-receptive pluripotent stem cell-derived hepatocytes comprising obtaining pluripotent stem cell (PSC)-derived hepatocytes and culturing the PSC-derived hepatocytes in media comprising cyclic adenosine monophosphate (cAMP) and a Janus kinase inhibitor (JAKi), thereby producing virus receptive hepatocytes.

In certain aspects, the cAMP and JAKi are cultured sequentially in different media. For example, the cAMP is administered in a first media and the JAKi is administered in a second media. In some aspects, cAMP is present in the medium from about 2 days to about 6 days. In certain aspects, the JAKi is present in the medium from about 1 day to about 3 days. In further aspects, the media is serum-free or defined media.

In some aspects, the pluripotent stem cell is human. In certain aspects, the pluripotent stem cell is an embryonic stem cell. In other aspects, the pluripotent stem cell is an induced pluripotent stem cell.

In certain aspects, the JAKi is 2-(1,1-Dimethylethyl)-9-fluoro-3,6-dihydro-7H-benz[h]-imidaz[4,5-f]isoquinolin-7-one (JAK Inhibitor 1), 1,2,3,4,5,6-Hexabromocyclohexane, or (E)-4,4'-(1,2-Diethyl-1,2-ethenediyl)bis[2-[(diethylamino)methyl]-phenol (9CI), 4,4'(3E)-Hex-3-ene-3,4-diyl-bis{2-[(diethylamino)methyl]phenol} (NSC33994). In some aspects, the JAKi is present at a concentration of about 0.1 µM to about 5 µM, such as 0.5 µM to 2.5 µM, such as 0.75 µM to 1.5 µM. In particular aspects, the JAKi is present at a concentration of about 1 µM.

In some aspects, the cAMP is present at a concentration of about 0.1 mM to about 3 mM, such as 0.5 µM to 2 µM. In particular aspects, the cAMP is present at a concentration of about 1 mM.

In certain aspects, the virus receptive hepatocytes have an increased expression of at least one hepatocyte maturation or viral infectivity gene relative to expression in the PSC-derived hepatocytes. In some aspects, the hepatocyte maturation or viral infectivity gene is selected from the group consisting of UGT1A1, PPARGC1A, TAT, PCK1, NR13, SLC10A1, GSTA2, GLYAT, and MT1M.

In further aspects, the virus receptive hepatocytes have an enhanced ability to support a hepatitis B virus (HBV) infection and/or a hepatitis C virus (HCV) infection relative to the PSC-derived hepatocytes.

In further embodiments, the virus receptive hepatocytes are infected with hepatitis B virus. In some aspects, the virus receptive hepatocytes have an increase in secretion of at least one HBV surface antigen. In particular aspects, the at least one HBV surface antigen is HBsAG or HBeAG. In certain aspects, the increase in surface antigen secretion is at least 2-fold relative to PSC-derived hepatocytes infected by HBV. In some aspects, the increase in surface antigen secretion is at least 5-fold relative to PSC-derived hepatocytes infected by HBV. In particular aspects, the increase in surface antigen secretion is at least 10-fold relative to PSC-derived hepatocytes infected by HBV. In some aspects, the virus receptive hepatocytes produce hepatitis B virus capable of infecting other virus receptive hepatocytes.

In even further embodiments, methods are provided for screening for a compound that inhibits HBV replication comprising obtaining virus receptive hepatocytes that have been infected by HBV, wherein said virus receptive hepatocytes are obtained by culturing PSC-derived hepatocytes in media comprising cyclic adenosine monophosphate (cAMP) and a Janus kinase inhibitor (JAKi), contacting said hepatocytes with a candidate compound, and measuring the level of HBV antigen secretion, wherein a decrease in HBV antigen secretion identifies a compound that inhibits HBV replication. In some aspects, the HBV antigen is HBsAG and/or HBeAG.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
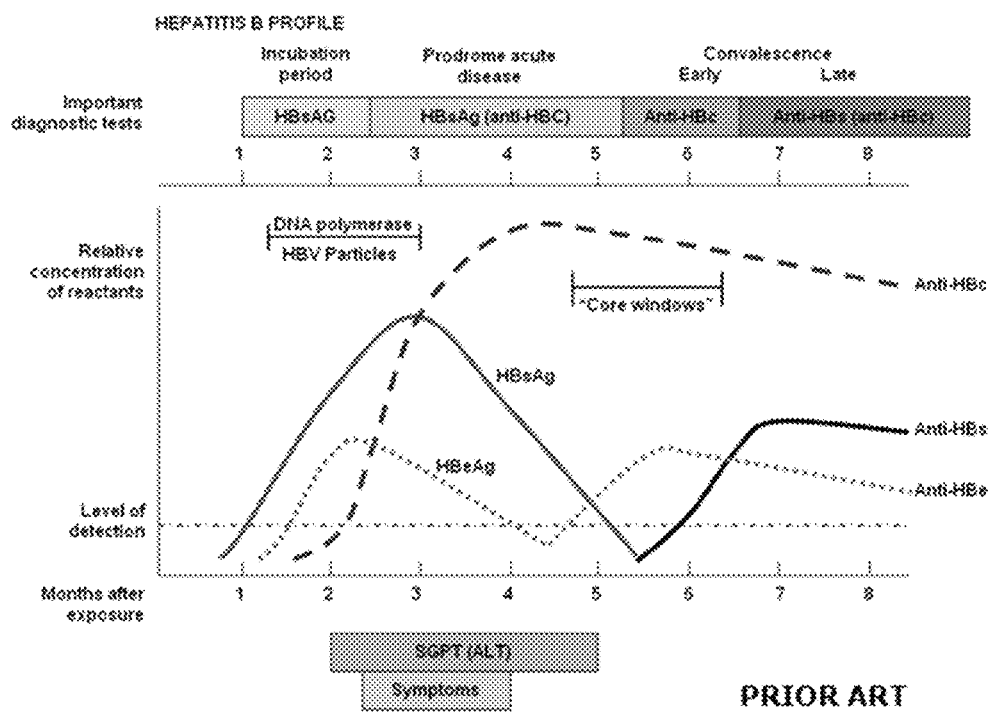
FIGS. 1A-1B: (A) Clinical progression of Hepatitis B Virus (HBV). The serological profile of HBV shows that the first indication of a HBV infection is the detection of the HBsAG in serum. HBsAG is present in the serum in up to $1\times10^6$-fold molar surplus of a live virus particle and therefore easy to detect. HBeAG is expressed by HBV infected cells later in the life cycle at lower quantities and generally used to confirm a true HBV infection in vivo. (B) Schematic showing life cycle of HBV with secretion of S-antigen and E-antigen (Nassal, et al., 2008).
Figure 1B:
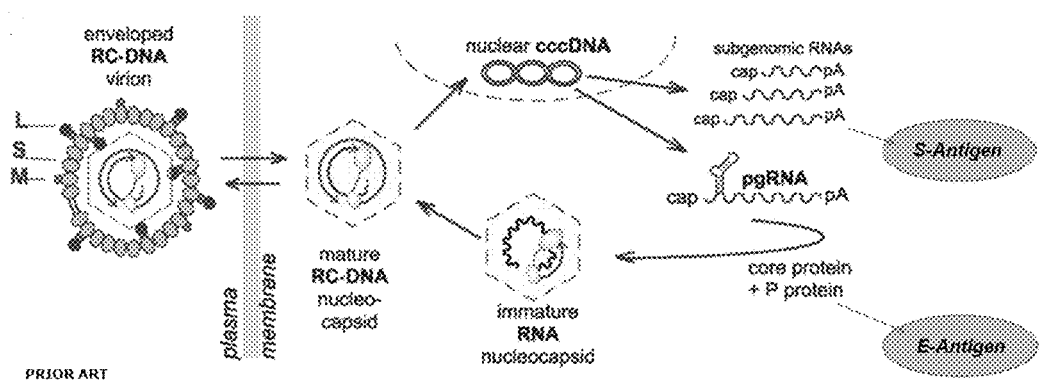

The present disclosure overcomes several major problems with current technologies for producing hepatocytes from pluripotent stem cells (PSC) that are receptive to virus infection, where a starting population of PSC-derived hepatocytes are simply cultured in the presence of a combination of compounds that dramatically increase virus receptivity of the resultant hepatocytes. Notably, the methods of the present disclosure apply to any type of pluripotent stem cells, including for example embryonic stem cells or induced pluripotent stem cells. In one example, PSC-derived hepatocytes are cultured in medium comprising cyclic adenosine monophosphate (cAMP) to initiate maturation and then cultured in medium comprising a Janus kinase inhibitor to complete the process to produce hepatocytes with enhanced virus receptivity particularly to HBV. In some embodiments, PSC-derived hepatocytes may be cultured in medium comprising both cAMP and JAKi. A useful means of characterizing the treated hepatocytes is by simply comparing the gene expression patterns of the PSC-derived hepatocytes to those of primary hepatocytes. Another approach is to assess the ability of the PSC-derived hepatocytes to maintain hepatitis B virus (HBV) replication (e.g., as characterized by secretion of surface antigens such as HBsAG and HBeAG) at increased levels as compared to HBV infectivity of the starting population of PSC-derived hepatocytes.

Accordingly, further embodiments provide methods of screening for candidate compounds that inhibit HBV replication. In certain aspects, the treated hepatocytes provided herein are infected with HBV and subsequently contacted with a test compound. In particular aspects, the secretion of HBV surface antigens such as HBsAG and HBeAG is measured and a decrease in antigen secretion identifies a candidate anti-HBV drug.

Thus, the methods of the present disclosure provide unlimited numbers of human hepatocytes receptive to virus infection for a wide range of applications that include model systems for the development of new treatments for a spectrum of diseases including hepatitis B virus infection and prevention of liver injury, the establishment of platforms for predictive toxicology, and the creation of in vitro models of disease. In addition, the methods described herein can be used to derive patient-specific functional hepatocytes for use in clinical applications of hepatocyte transplantation to restore a degree of liver function to a subject needing such therapy, perhaps due to an acute, chronic, or inherited impairment of liver function.

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The term "cell" is herein used in its broadest sense in the art and refers to a living body that is a structural unit of tissue of a multicellular organism, is surrounded by a membrane structure that isolates it from the outside, has the capability of self-replicating, and has genetic information and a mechanism for expressing it. Cells used herein may be naturally-occurring cells or artificially modified cells (e.g., fusion cells, genetically modified cells, etc.).

The term "stem cell" refers herein to a cell that under suitable conditions is capable of differentiating into a diverse range of specialized cell types, while under other suitable conditions is capable of self-renewing and remaining in an essentially undifferentiated pluripotent state. The term "stem cell" also encompasses a pluripotent cell, multipotent cell, precursor cell and progenitor cell. Exemplary human stem cells can be obtained from hematopoietic or mesenchymal stem cells obtained from bone marrow tissue, embryonic stem cells obtained from embryonic tissue, or embryonic germ cells obtained from genital tissue of a fetus. Exemplary pluripotent stem cells can also be produced from somatic cells by reprogramming them to a pluripotent state by the expression of certain transcription factors associated with pluripotency; these cells are called "induced pluripotent stem cells" or "iPSCs".

An "embryonic stem (ES) cell" is an undifferentiated pluripotent cell which is obtained from an embryo in an early stage, such as the inner cell mass at the blastocyst stage, or produced by artificial means (e.g. nuclear transfer) and can give rise to any differentiated cell type in an embryo or an adult, including germ cells (e.g. sperm and eggs).

"Induced pluripotent stem cells (iPSCs)" are cells generated by reprogramming a somatic cell by expressing or inducing expression of a combination of factors (herein referred to as reprogramming factors). iPSCs can be generated using fetal, postnatal, newborn, juvenile, or adult somatic cells. In certain embodiments, factors that can be used to reprogram somatic cells to pluripotent stem cells include, for example, Oct4 (sometimes referred to as Oct 3/4), Sox2, c-Myc, Klf4, Nanog, and Lin28. In some embodiments, somatic cells are reprogrammed by expressing at least two reprogramming factors, at least three reprogramming factors, or four reprogramming factors to reprogram a somatic cell to a pluripotent stem cell.

"Reprogramming" is a process that confers on a cell a measurably increased capacity to form progeny of at least one new cell type, either in culture or in vivo, than it would have under the same conditions without reprogramming. More specifically, reprogramming is a process that confers on a somatic cell a pluripotent potential. This means that after sufficient proliferation, a measurable proportion of progeny have phenotypic characteristics of the new cell type if essentially no such progeny could form before reprogramming; otherwise, the proportion having characteristics of the new cell type is measurably more than before reprogramming. Under certain conditions, the proportion of progeny with characteristics of the new cell type may be at least about 0.05%, 0.1%, 0.5%, 1%, 5%, 25% or more in order of increasing preference.

"Pluripotent stem cell" refers to a stem cell that has the potential to differentiate into all cells found in an organism preferably, cells representing any of the three germ layers: endoderm (interior stomach lining, gastrointestinal tract, the lungs), mesoderm (muscle, bone, blood, urogenital), or ectoderm (epidermal tissues and nervous system).

As used herein, the term "somatic cell" refers to any cell other than germ cells, such as an egg or a sperm, which does not directly transfer its DNA to the next generation. Typically, somatic cells have limited or no pluripotency. Somatic cells used herein may be naturally-occurring or genetically modified.

As used herein the term "engineered" in reference to cells refers to cells that comprise at least one genetic element exogenous to the cell that is integrated into the cell genome. In some aspects, the exogenous genetic element can be integrated at a random location in the cell genome. In other aspects, the genetic element is integrated at a specific site in the genome. For example, the genetic element may be integrated at a specific position to replace an endogenous nucleic acid sequence, such as to provide a change relative to the endogenous sequence (e.g., a change in single nucleotide position).

The term "defined" or "fully defined," when used in relation to a medium, an extracellular matrix, or a culture condition, refers to a medium, an extracellular matrix, or a culture condition in which the chemical composition and amounts of approximately all the components are known. For example, a defined medium does not contain undefined factors such as in fetal bovine serum, bovine serum albumin or human serum albumin. Generally, a defined medium comprises a basal media (e.g., Dulbecco's Modified Eagle's Medium (DMEM), F12, or Roswell Park Memorial Institute Medium (RPMI) 1640, containing amino acids, vitamins, inorganic salts, buffers, antioxidants and energy sources) which is supplemented with recombinant albumin, chemically defined lipids, and recombinant insulin.

The term "hepatocyte" as used herein is meant to include hepatocyte-like cells that exhibit some but not all characteristics of mature hepatocytes, as well as mature and fully functional hepatocytes which have all characteristics of hepatocytes as determined by morphology, marker expression, and in vitro and in vivo functional assays.

The terms "JAKi", "JAK inhibitor", and "JAK/STAT inhibitor" are used interchangeably herein to refer to any agent capable of down-regulating or otherwise decreasing or suppressing the amount and/or activity of JAK-STAT interactions. JAK inhibitors down-regulate the quantity or activity of JAK molecules. STAT inhibitors down-regulate the quantity or activity of STAT molecules. Inhibition of these cellular components can be achieved by a variety of mechanisms known in the art, including, but not limited to binding directly to JAK (e.g., a JAK-inhibitor compound binding complex, or substrate mimetic), binding directly to STAT, or inhibiting the expression of the gene, which encodes the cellular components. JAK/STAT inhibitors, for example, are disclosed in U.S. Patent Publication No. 2004/0209799, PCT Publication No. WO2014013014, PCT Publication No. WO2009155551, and U.S. Pat. No. 9,133,200, all incorporated herein by reference.

The term "drug" or "candidate compound" refers to a molecule including, but not limited to, small molecules, nucleic acids and proteins or combinations thereof that alter or are candidates for altering a phenotype associated with disease.

An "anti-HBV agent" is defined herein as a compound or composition that interferes with the replication of HBV in vitro or in vivo.

"High-throughput screening" refers to methods for simultaneously assaying a large number of test compounds for their ability to inhibit viral replication, particularly HBV replication. In general, these methods take advantage of automated equipment.

II. PRODUCTION OF MATURING HEPATOCYTES

A. Starting Population of Hepatocytes

In certain embodiments of the present disclosure, there are disclosed methods and compositions for producing virus-receptive hepatocytes, particularly receptive to HBV, by culturing a starting population of hepatocytes under conditions that increase their maturity so as to acquire the ability to exhibit characteristics of chronic viral (e.g., HBV) infection. Primary hepatocytes obtained from donors are mature hepatocytes and are receptive to HBV infection. The starting population of hepatocytes may be pluripotent stem cell (PSC)-derived hepatocytes or primary hepatocytes. But for PSC-derived hepatocytes to become fully receptive to chronic HBV infection, they require a certain level of maturation approaching that of primary hepatocytes and the methods described herein provide a certain level of such maturation so as to acquire receptivity to chronic HBV infection. In some embodiments, the starting population of hepatocytes may be stem cell-derived, including but are not limited to, induced pluripotent stem cells and embryonic stem cells.

1. Pluripotent Stem Cells

The starting population of PSC-derived hepatocytes can be derived from human embryonic stem cells (ESCs) and induced pluripotent stem cells (iPSC). Both ESCs and iPSCs are capable of long-term proliferation in vitro, while retaining the potential to differentiate into all cell types of the body, including hepatocytes. The starting populations of human ESC- and iPSC-derived hepatocytes generally do not exhibit the full functional spectrum of human primary adult hepatocytes. Certain aspects of the present disclosure concern a starting population of PSC-derived hepatocytes that could be induced directly from human ESC or iPSCs via expression of a combination of transcription factors important for hepatocyte differentiation/function, similar to the generation of iPSCs, bypassing most, if not all, normal developmental stages (U.S. Pat. No. 8,481,317; U.S. Patent Publication No. 20140242595; PCT/US2015/026583).

a. Embryonic Stem Cells

In certain aspects, the starting population of hepatocytes is derived from embryonic stem cells. ES cells are derived from the inner cell mass of blastocysts and have a high in vitro differentiating capability. ES cells can be isolated by removing the outer trophectoderm layer of a developing embryo, then culturing the inner mass cells on a feeder layer of non-growing cells. The replated cells can continue to proliferate and produce new colonies of ES cells which can be removed, dissociated, replated again and allowed to grow. This process of "subculturing" undifferentiated ES cells can be repeated a number of times to produce cell lines containing undifferentiated ES cells (U.S. Pat. Nos. 5,843,780; 6,200,806; 7,029,913). ES cells have the potential to proliferate while maintaining their pluripotency. For example, ES cells are useful in research on cells and on genes which control cell differentiation. The pluripotency of ES cells combined with genetic manipulation and selection can be used for gene analysis studies in vivo via the generation of transgenic, chimeric, and knockout mice.

Methods for producing mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be produced or derived from a zygote or blastocyst-staged mammalian embryo produced by the fusion of a sperm and egg cell, nuclear transfer, pathogenesis, or the reprogramming of chromatin and subsequent incorporation of the reprogrammed chromatin into a plasma membrane to produce an embryonic cell by previously described methods (Thomson and Marshall, 1998; Reubinoff et al., 2000). In one method, human blastocysts are exposed to anti-human serum, and trophectoderm cells are lysed and removed from the inner cell mass which is cultured on a feeder layer of mouse embryonic fibroblasts. Further, clumps of cells derived from the inner cell mass are chemically or mechanically dissociated, replated, and colonies with undifferentiated morphology are selected by micropipette, dissociated, and replated. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as MATRIGEL™ or laminin in the presence of "conditioned" medium containing basic fibroblast growth factor (Xu et al., 2001).

ES cells can also be derived from other organisms including rhesus monkey and marmoset by previously described methods (Thomson, and Marshall, 1998; Thomson et al., 1995; Thomson and Odorico, 2000; U.S. Pat. No. 5,843,780), as well as from established mouse and human cell lines. For example, established human ES cell lines include MAOI, MA09, ACT-4, HI, H7, H9, H13, H14 and ACT30. As a further example, mouse ES cell lines that have been established include the CGR8 cell line established from the inner cell mass of the mouse strain 129 embryos, and cultures of CGR8 cells can be grown in the presence of LIF without feeder layers.

ES stem cells can be detected by protein markers including transcription factor Oct4, alkaline phosphatase (AP), stage-specific embryonic antigen SSEA-1, stage-specific embryonic antigen SSEA-3, stage-specific embryonic antigen SSEA-4, transcription factor NANOG, tumor rejection antigen 1-60 (TRA-1-60), tumor rejection antigen 1-81 (TRA-1-81), SOX2, or REX1.

b. Induced Pluripotent Stem Cells

In other aspects, the starting population of hepatocytes are derived from induced pluripotent stem cells, commonly abbreviated iPS cells or iPSCs. The induction of pluripotency was originally achieved in 2006 using mouse cells (Yamanaka et al. 2006) and in 2007 using human cells (Yu et al. 2007; Takahashi et al. 2007) by reprogramming of somatic cells via the introduction of transcription factors that are linked to pluripotency. The use of iPSCs circumvents most of the ethical and practical problems associated with large-scale clinical use of ES cells, and patients with iPSC-derived autologous transplants may not require lifelong immunosuppressive treatments to prevent graft rejection.

With the exception of certain cell types (such as germ cells and enucleated erythrocytes), any cell can be used as a starting point for iPSCs. For example, cell types could be keratinocytes, fibroblasts, hematopoietic cells, mesenchymal cells, liver cells, or stomach cells. T cells may also be used as a source of somatic cells for reprogramming (published US patent application 20140315304; U.S. Pat. No. 8,741,648). There is no limitation on the degree of cell differentiation or the age of an animal from which cells are collected; even undifferentiated progenitor cells (including somatic stem cells) and finally differentiated mature cells can be used as sources of somatic cells in the methods disclosed herein. In one embodiment, the somatic cell is itself a blood cell such as a human CD34+ hematopoietic progenitor cell or a skin cells such as a human fibroblast. The somatic cell can be an adult or a fetal somatic cell. iPSCs can be grown under conditions that are known to differentiate human ES cells into specific cell types, and express human ES cell markers including: SSEA-1, SSEA-3, SSEA-4, TRA-1-60, and TRA-1-81.

Somatic cells can be reprogrammed to produce induced pluripotent stem cells (iPSCs) using methods known to one of skill in the art. One of skill in the art can readily produce induced pluripotent stem cells, see for example, Published U.S. Patent Application No. 20090246875, Published U.S. Patent Application No. 2010/0210014; Published U.S. Patent Application No. 20120276636; U.S. Pat. No. 8,058,065; U.S. Pat. No. 8,129,187; PCT Publication NO. WO 2007/069666 A1, and U.S. Pat. No. 8,268,620, which are incorporated herein by reference. Generally, nuclear reprogramming factors are used to produce pluripotent stem cells from a somatic cell. In some embodiments, at least three, or at least four, of Klf4, c-Myc, Oct3/4, Sox2, Nanog, and Lin28 are utilized. In other embodiments, Oct3/4, Sox2 and at least one of Nanog and Lin28 are utilized. In other embodiments, Oct3/4, Sox2 and at least one of c-Myc and Klf4 are utilized.

Mouse and human cDNA sequences of these nuclear reprogramming substances are available with reference to the NCBI accession numbers mentioned in U.S. Pat. No. 8,183,038 and WO 2007/069666, which are incorporated herein by reference. Methods for introducing one or more reprogramming substances, or nucleic acids encoding these reprogramming substances, are known in the art, and disclosed for example, in published U.S. Pat. Nos. 8,268,620, 8,691,574, 8,741,648, 8,546,140, 8,900,871 and 8,071,369, which are incorporated herein by reference.

Once derived, iPSCs can be cultured in a medium sufficient to maintain pluripotency. The iPSCs may be used with various media and techniques developed to culture pluripotent stem cells, more specifically, embryonic stem cells, as described in U.S. Pat. No. 7,442,548 and U.S. Patent Pub. No. 2003/0211603. In the case of mouse cells, the culture is carried out with the addition of Leukemia Inhibitory Factor (LIF) as a differentiation suppression factor to an ordinary medium. In the case of human cells, it is desirable that basic fibroblast growth factor (bFGF) be added in place of LIF. Other methods for the culture and maintenance of iPSCs, as would be known to one of skill in the art, may be used with the present methods.

In certain embodiments, undefined conditions may be used; for example, pluripotent cells may be cultured on fibroblast feeder cells or a medium that has been exposed to fibroblast feeder cells in order to maintain the stem cells in an undifferentiated state. In some embodiments, the cell is cultured in the co-presence of mouse embryonic fibroblasts treated with radiation or an antibiotic to terminate the cell division, as feeder cells. Alternately, pluripotent cells may be cultured and maintained in an essentially undifferentiated state using a defined, feeder-independent culture system, such as a TESR™ medium (Ludwig et al., 2006a; Ludwig et al., 2006b) or E8™/Essential 8™ medium (Chen et al., 2011).

Plasmids have been designed with a number of goals in mind, such as achieving regulated high copy number and avoiding potential causes of plasmid instability in bacteria, and providing means for plasmid selection that are compatible with use in mammalian cells, including human cells. Particular attention has been paid to the dual requirements of plasmids for use in human cells. First, they are suitable for maintenance and fermentation in *E. coli*, so that large amounts of DNA can be produced and purified. Second, they are safe and suitable for use in human patients and animals. The first requirement calls for high copy number plasmids that can be selected for and stably maintained relatively easily during bacterial fermentation. The second requirement calls for attention to elements such as selectable markers and other coding sequences. In some embodiments plasmids that encode a marker are composed of: (1) a high copy number replication origin, (2) a selectable marker, such as, but not limited to, the neo gene for antibiotic selection with kanamycin, (3) transcription termination sequences, including the tyrosinase enhancer and (4) a multicloning site for incorporation of various nucleic acid cassettes; and (5) a nucleic acid sequence encoding a marker operably linked to the tyrosinase promoter. There are numerous plasmid vectors that are known in the art for inducing a nucleic acid encoding a protein. These include, but are not limited to, the vectors disclosed in U.S. Pat. No. 6,103,470; U.S. Pat. No. 7,598,364; U.S. Pat. No. 7,989,425; and U.S. Pat. No. 6,416,998, which are incorporated herein by reference.

An episomal gene delivery system can be a plasmid, an Epstein-Barr virus (EBV)-based episomal vector (U.S. Pat. No. 8,546,140), a yeast-based vector, an adenovirus-based vector, a simian virus 40 (SV40)-based episomal vector, a bovine papilloma virus (BPV)-based vector, or a lentiviral vector. A viral gene delivery system can be an RNA-based or DNA-based viral vector (PCT/JP2009/062911).

c. Embryonic Stem Cells Derived by Somatic Cell Nuclear Transfer

Pluripotent stem cells for deriving the starting population of hepatocytes could also be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque ooctyes by electrofusion (Byrne et al., 2007). The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo.

2. Programming Factors for PSC-Derived Hepatocytes

Certain aspects of the present disclosure concern a starting population of iPSC-derived hepatocytes produced by hepatocyte programming factors for hepatocyte forward programming. The hepatocytes could be produced directly from PSCs by increasing the level of hepatocyte programming factors in the cells (U.S. Pat. No. 8,481,317; U.S. Patent Publication No. 20140242595; PCT/US2015/026583, incorporated herein by reference). The numerous functions of hepatocytes could be controlled at the transcriptional level by the concerted actions of a limited number of hepatocyte-enriched transcription factors. Any transcription factors important for hepatocyte differentiation or function may be used to produce the starting population of PSC-derived hepatocytes described herein, like hepatocyte-enriched transcription factors, particularly the genes thereof listed in Table 1.

For example, by effecting expression of a combination of transcription factors in Table 1, forward programming into hepatocytes from pluripotent stem cells may be used to obtain PSC-derived hepatocytes. For example, the PSC-derived hepatocytes can be derived by a combination of the following transcription factors: FOXA2, HHEX, HNF1A, GATA4, MAFB, and TBX3.

B. Methods of Producing Mature Hepatocytes

Embodiments of the present disclosure provide methods of producing virus-receptive hepatocytes particularly receptivity to HBV infection, by increasing the maturation status of the hepatocytes. The hepatocytes of the embodiments can be made by culturing pluripotent stem cell (PSC)-derived hepatocytes or primary hepatocytes in a medium under specific maturation culture conditions that increase the receptivity of the hepatocytes to virus infection. The medium may contain two or more agents that enhance virus receptivity including agents that enhance hepatocyte maturation.

After the starting population of PSC-derived hepatocytes has adhered to the culture plate, the cells are preferably cultured in Plating Medium. The Plating Medium can comprise culture media such as RPMI 1640 and Oncostatin M. The Plating Medium can additionally comprise B27 supplement, dexamethasone, gentamycin and a hepatocyte medium supplement such as iCell® Hepatocyte 2.0 medium supplement. One exemplary Plating Medium is shown in Table 3.

After the cells are cultured in the Plating Medium for about 24 hours, the cells are then cultured in Plating Medium

TABLE 1

A list of candidate genes for direct programming of human ESC or iPSCs to hepatocytes.

| # | Symbol | Entrez Gene ID | Accession | Name |
|---|---|---|---|---|
| 1 | FOXA1 | 3169 | NM_004496 | forkhead box A1 |
| 2 | FOXA2 | 3170 | NM_021784 | forkhead box A2 isoform 1 |
|   |   |   | NM_153675 | forkhead box A2 isoform 2 |
| 3 | FOXA3 | 3171 | NM_004497 | forkhead box A3 |
| 4 | GATA4 | 2626 | NM_002052 | GATA binding protein 4 |
| 5 | HHEX | 3087 | NM_002729 | hematopoietically expressed homeobox |
| 6 | TBX3 | 6926 | NM_005996 | T-box 3 isoform 1 |
|   |   |   | NM_016569 | T-box 3 isoform 2 |
| 7 | HNF1A | 6927 | NM_000545 | HNF1 homeobox A |
| 8 | HNF4A | 3172 | NM_000457 | hepatocyte nuclear factor 4, alpha |
| 9 | MAFB | 9935 | NM_005461 | v-maf musculoaponeurotic fibrosarcoma oncogene homolog B (avian) |
| 10 | ABLIM3 | 22885 | NM_014945 | actin binding LIM protein family, member 3 |
| 11 | AHR | 196 | NM_001621 | aryl hydrocarbon receptor |
| 12 | AR | 367 | NM_000044 | androgen receptor |
| 13 | ATF5 | 22809 | NM_012068 | activating transcription factor 5 |
| 14 | ATOH8 | 84913 | NM_032827 | atonal homolog 8 (*Drosophila*) |
| 15 | ESR1 | 2099 | NM_000125 | estrogen receptor 1 |
| 16 | NF1A | 4774 | NM_001134673 | nuclear factor I/A |
| 17 | NF1B | 4781 | NM_005596 | nuclear factor I/B |
| 18 | NR0B2 | 8431 | NM_021969 | nuclear receptor subfamily 0, group B, member 2 |
| 19 | NR1H4 | 9971 | NM_005123 | nuclear receptor subfamily 1, group H, member 4 |
| 20 | NR1I2 | 8856 | NM_003889 | nuclear receptor subfamily 1, group I, member 2, isoform 1 |
|   |   |   | NM_022002 | nuclear receptor subfamily 1, group I, member 2, isoform 2 |
| 21 | NR1I3 | 9970 | NM_001077482 | nuclear receptor subfamily 1, group I, member 3, transcript variant 1 |
| 22 | NR3C2 | 4306 | NM_000901 | nuclear receptor subfamily 3, group C, member 2 |
| 23 | NR5A2-2 | 2494 | NM_003822 | nuclear receptor subfamily 5, group A, member 2 |
| 24 | PPARA | 5465 | NM_005036 | PPARA peroxisome proliferator-activated receptor alpha |
| 25 | PROX1 | 5629 | NM_002763 | prospero homeobox 1 |
| 26 | RORC | 6097 | NM_005060 | RAR-related orphan receptor C |
| 27 | SCML1 | 6322 | NM_001037540 | sex comb on midleg-like 1 (*Drosophila*) isoform a |
|   |   |   | NM_006746 | sex comb on midleg-like 1 (*Drosophila*) isoform b |
|   |   |   | NM_001037535 | sex comb on midleg-like 1 (*Drosophila*) isoform c |
| 28 | THRB | 7068 | NM_000461 | thyroid hormone receptor, beta (erythroblastic leukemia viral (v-erb-a) oncogene homolog 2, avian) |
| 29 | ZIC1 | 7545 | NM_003412 | Zic family member 1 (odd-paired homolog, *Drosophila*) | with an agent to initiate virus receptivity. In certain aspects, during at least part of the maturation process, the hepatocytes are cultured in the presence of cyclic adenosine monophosphate (cAMP). The cAMP may be used at an effective concentration of at least or about 0.1 mM to about 10 mM, such as about 1 mM cAMP. The hepatocytes are generally cultured in the Plating Medium with cAMP for about 1 to about 6 days, such as about 1, 2, 3, 4 or 5 days, such as for about 4 days to produce cAMP-treated hepatocytes. The medium is aspirated each day and replaced with fresh Plating Medium with cAMP.

To complete the maturation process, the cAMP cultured hepatocytes are then cultured in Maintenance Medium supplemented with one or more Janus kinase inhibitors. The Janus kinase inhibitor may be used at an effective concentration of at least or about 0.02, 0.05, 0.1, 0.2, 0.5, 1, 2, 3, 4, 5, 10, 15, 20, 25, to about 30 µM, or any range derivable therein. Preferably, the Janus kinase inhibitor may be used at an effective concentration of about 0.1 to about 5 µM, such as about 1 µM. The cells are generally cultured in the Maintenance Medium with a JAK inhibitor for about 1 to about 6 days, such as about 1, 2, 3, 4 or 5 days, such as for about 2 days to produce virus receptive hepatocytes. The medium is aspirated each day and replaced with fresh Maintenance Medium with JAKi. The resulting cAMP and JAKi treated hepatocytes can then be characterized by methods disclosed herein such as evaluating receptivity to hepatitis B infection.

Alternatively, PSC-derived hepatocytes that have been cultured for about 24 hours can then be cultured in medium, such as Maintenance Medium or Plating Medium, supplemented with cAMP and one or more JAK inhibitors. The cAMP may be used at an effective concentration of at least or about 0.1 mM to about 10 mM, such as about 1 mM cAMP. The Janus kinase inhibitor may be used at an effective concentration of at least or about 0.02, 0.05, 0.1, 0.2, 0.5, 1, 2, 3, 4, 5, 10, 15, 20, 25, to about 30 µM, or any range derivable therein. Preferably, the Janus kinase inhibitor may be used at an effective concentration of about 0.1 to about 5 µM, such as about 1 µM. The cells may be cultured in medium, such as Maintenance Medium or Plating Medium, with cAMP and a JAK inhibitor for about 1 to about 6 days, such as about 1, 2, 3, 4 or 5 days to produce virus receptive hepatocytes. The medium is aspirated each day and replaced with fresh medium, such as Maintenance Medium or Plating Medium, with cAMP and JAKi. The resulting cAMP and JAKi treated hepatocytes can then be characterized by methods disclosed herein such as evaluating receptivity to hepatitis B infection.

1. Cell Culture

Generally, cells of the present disclosure are cultured in a culture medium, which is a nutrient-rich buffered solution capable of sustaining cell growth. However, the starting immature hepatocytes and the ending maturing virus-receptive hepatocytes may have differing requirements for culture medium and conditions.

Culture media suitable for isolating, expanding, and differentiating stem cells into hepatocytes to obtain the starting population of PSC-derived hepatocytes described herein include, but are not limited, to high glucose Dulbecco's Modified Eagle's Medium (DMEM), DMEM/F-15, Liebovitz L-15, RPMI 1640, Iscove's modified Dulbecco's media (IMDM), and Opti-MEM SFM (Invitrogen Inc.). Chemically Defined Medium comprises a minimum essential medium such as Iscove's Modified Dulbecco's Medium (IMDM) (Gibco), supplemented with human serum albumin, human EXCYTE™ lipoprotein, transferin, insulin, vitamins, essential and non-essential amino acids, sodium pyruvate, glutamine and a mitogen is also suitable. As used herein, a mitogen refers to an agent that stimulates cell division of a cell. An agent can be a chemical, usually some form of a protein that encourages a cell to commence cell division, triggering mitosis. In one embodiment, serum-free media, such as those described in U.S. Pat. No. 5,908,782 and WO96/39487, and the "complete media" as described in U.S. Pat. No. 5,486,359 are contemplated for use with the method described herein. In some embodiments, the culture medium is supplemented with 10% Fetal Bovine Serum (FBS), human autologous serum, human AB serum or platelet rich plasma supplemented with heparin (2 U/ml).

The medium for culturing the hepatocytes of the present disclosure can also contain fatty acids or lipids, amino acids (such as non-essential amino acids), vitamin(s), growth factors, cytokines, antioxidant substances, 2-mercaptoethanol, pyruvic acid, buffering agents, and inorganic salts. The concentration of 2-mercaptoethanol can be, for example, about 0.05 to 1.0 mM, and particularly about 0.1 to 0.5 mM, but the concentration is particularly not limited thereto as long as it is appropriate for culturing the hepatocytes.

A culture vessel used for culturing the stem cell(s) can include, but is particularly not limited to: flask, flask for tissue culture, dish, petri dish, dish for tissue culture, multi dish, micro plate, micro-well plate, multi plate, multi-well plate, micro slide, chamber slide, tube, tray, CELLSTACK® Chambers, culture bag, and roller bottle, as long as it is capable of culturing the stem cells therein. The stem cells may be cultured in a volume of at least or about 0.2, 0.5, 1, 2, 5, 10, 20, 30, 40, 50 ml, 100 ml, 150 ml, 200 ml, 250 ml, 300 ml, 350 ml, 400 ml, 450 ml, 500 ml, 550 ml, 600 ml, 800 ml, 1000 ml, 1500 ml, or any range derivable therein, depending on the needs of the culture. In a certain embodiment, the culture vessel may be a bioreactor, which may refer to any device or system that supports a biologically active environment. The bioreactor may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

The culture vessel can be cellular adhesive or non-adhesive and selected depending on the purpose. The cellular adhesive culture vessel can be coated with any of substrates for cell adhesion such as extracellular matrix (ECM) to improve the adhesiveness of the vessel surface to the cells. The substrate for cell adhesion can be any material intended to attach stem cells or feeder cells (if used). The substrate for cell adhesion includes collagen, gelatin, poly-L-lysine, poly-D-lysine, vitronectin, laminin, fibronectin, and RetroNectin and mixtures thereof for example MATRIGEL™, and lysed cell membrane preparations (Klimanskaya et al., 2005).

Other culturing conditions can be appropriately defined. For example, the culturing temperature can be about 30 to 40° C., for example, at least or about 31, 32, 33, 34, 35, 36, 37, 38, 39° C. but particularly not limited to them. The $CO_2$ concentration can be about 1 to 10%, for example, about 2 to 5%, or any range derivable therein. The oxygen tension can be at least or about 1, 5, 8, 10, 20%, or any range derivable therein.

Pluripotent stem cells to be differentiated into the starting population of PSC-hepatocytes may be cultured in a medium sufficient to maintain the pluripotency. Culturing of induced pluripotent stem (iPS) cells generated in certain aspects of the present disclosure can use various medium and techniques developed to culture primate pluripotent stem cells, more specially, embryonic stem cells, as described in U.S.

Pat. No. 7,442,548 and U.S. Pat. App. 20030211603. For example, like human embryonic stem (hES) cells, iPS cells can be maintained in 80% DMEM (Gibco #10829-018 or #11965-092), 20% defined fetal bovine serum (FBS) not heat inactivated, 1% non-essential amino acids, 1 mM L-glutamine, and 0.1 mM beta-mercaptoethanol. Alternatively, ES cells can be maintained in serum-free medium, made with 80% Knock-Out DMEM (Gibco #10829-018), 20% serum replacement (Gibco #10828-028), 1% non-essential amino acids, 1 mM L-glutamine, and 0.1 mM beta-mercaptoethanol. Just before use, human bFGF may be added to a final concentration of about 4 ng/mL (WO 99/20741).

2. Janus Kinase Inhibitors

Certain aspects of the present disclosure concern a Janus kinase inhibitor as a factor to enhance virus receptivity in hepatocytes. The Janus Kinase (JAK) family plays a role in the cytokine-dependent regulation of proliferation and function of cells involved in immune response. Currently, there are four known mammalian JAK family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2). The JAK proteins range in size from 120 to 140 kDa and comprise seven conserved JAK homology (JH) domains; one of these is a functional catalytic kinase domain, and another is a pseudokinase domain potentially serving a regulatory function and/or serving as a docking site for STATs (Scott, Godshall et al. 2002).

Examples of JAK/STAT inhibitors which may be useful in the present methods include, but are not limited to: PIAS proteins, which bind and inhibit at the level of the STAT proteins (Chung et al. Science, 1997); members of an SH2 containing family of proteins, which are able to bind to JAKs and/or receptors and block signaling (see, for example, Aman and Leonard, 1997, Nicholson and Hilton, 1998); cytokine-inducible Src homology 2-containing (CIS) protein, an inhibitor of STAT signaling (Yoshimura et al., 1995); CIS-related proteins, which can inhibit STAT signaling or directly bind to Janus kinases; Suppressor of Cytokine Signaling-I protein (SOCS-1, also referred to as JAB or SSI-1), which appears to associate with all JAKs to block the downstream activation of STAT3 (Ohya et al., 1997); Tyrphostins, which are derivatives of benzylidene malononitrile, resembling tyrosine and erbstatin moieties (Gazit et al. 1989); AG-490, a member of the tyrophostin family of tyrosine kinase inhibitors (Wang et al. 1999), 4,5-dimethoxy-2-nitrobenzoic acid and 4,5-dimethoxy-2-nitrobenzamide, which specifically inhibit JAK3; 4-(phenyl)-amino-6,7-dimethoxyquinazoline (parent compound WHI-258) and derivatives of this compound which are structurally-derived from dimethoxyquinazoline compounds; compounds containing a 4'-OH group, including 4-(4'-hydroxyphenyl)-amino-6,7-dimethoxyquinazoline (WHI-P131), 4-(3'-bromo-4'-hydroxylphenyl)-amino-6,7-dimethoxyquinazoline (WHI-P154), and 4-(3',5'-dibromo-4'-hydroxylphenyl)-amino-6,7-dimethoxyquinazoline (WHI-P97); WHI-P180, another dimethoxyquinazoline compound; and cAMP elevating agents, such as forskolin, a direct activator of adenylate cyclase and dibutyryl cAMP, and 3-isobutyl-1-methylxanthine (IBMX), an inhibitor of cAMP phosphodiesterase. Preferably, the JAK inhibitor is 2-(1,1-Dimethylethyl)-9-fluoro-3,6-dihydro-7H-benz[h]-imidaz[4,5-f]isoquinolin-7-one (JAK Inhibitor 1; EMD Millipore, Catolog #420099).

3. Cyclic Adenosine Monophosphate

Certain embodiments concern cyclic adenosine monophosphate as a factor for enhancing virus receptivity in hepatocytes by further maturing the cells. Cyclic adenosine monophosphate (cAMP, cyclic AMP, or 3',5'-cyclic adenosine monophosphate) is a second messenger important in many biological processes. cAMP is derived from adenosine triphosphate (ATP) and used for intracellular signal transduction in many different organisms, conveying the cAMP-dependent pathway. cAMP is synthesized from ATP by adenylate cyclase located on the inner side of the plasma membrane and anchored at various locations in the interior of the cell. Adenylate cyclase is activated by a range of signaling molecules through the activation of adenylate cyclase stimulatory G (Gs)-protein-coupled receptors. Adenylate cyclase is inhibited by agonists of adenylate cyclase inhibitory G (Gi)-protein-coupled receptors. Liver adenylate cyclase responds more strongly to glucagon, and muscle adenylate cyclase responds more strongly to adrenaline.

cAMP or a salt thereof can be used in the methods of the present disclosure. For example, adenosine 3',5'-cyclic monophosphate sodium salt monohydrate or adenosine 3',5'-cyclic monophosphate sodium salt monohydrate can be used for the production of virus-receptive hepatocytes.

4. Characterization of Virus-Receptive Hepatocytes

The treated hepatocytes of the present disclosure can be characterized according to a number of phenotypic and/or functional criteria. The criteria include but are not limited to receptivity to viral infection such as HBV infection, the detection or quantitation of expressed cell markers, enzymatic activity, and the characterization of morphological features and intercellular signaling.

a. Permissiveness to Viral Infection iCell Hepatocytes that have not been treated with cAMP and a JAKi are receptive to HCV infection as determined by contacting untreated hepatocytes with a source of infectious HCV particles and detecting that viral particle uptake is inhibited in a dose-dependent fashion by an anti-CD81 blocking antibody (Mann et al., 2013; incorporated herein by reference). However, receptivity to chronic HBV infection requires further maturation of the iCell Hepatocytes by culturing them in cAMP and a JAKi of the present disclosure. One feature of the treated hepatocytes of the present disclosure is that they are or may be susceptible or may exhibit susceptibility comparable to primary hepatocytes to certain pathogenic agents that are tropic for primary primate liver cells. Such pathogenic agents include hepatitis A, B, C, and delta, Epstein-Barr virus (EBV), cytomegalovirus (CMV), tuberculosis, and malaria. For example, receptivity to infection by hepatitis B virus can be determined by contacting agent treated hepatocytes with a source of infectious hepatitis B particles, such as serum from a human HBV carrier, and subsequently characterizing the HBV infection including secretion of HBV surface antigens and HBV replication by the production of HBV capable of reinfecting hepatocytes.

Accordingly, the hepatocytes produced by the methods of the present disclosure can be infected with hepatitis B virus for characterization. Usually, the Maintenance Media can be aspirated and replaced with Infection Medium. The Infection Medium comprises HBV particles and can additionally comprise Maintenance Media containing a JAKi and polyethylene glycol. After the mature hepatocytes have been infected with HBV, such as for about 12 hours to about 2 days, such as for about 24 hours, the media is aspirated and replaced with Maintenance Media with or without JAKi.

The HBV infection of the treated hepatocytes can be characterized by monitoring the levels of HBV antigen secretion or HBV cDNA throughout the viral life cycle such as up to 15 days after infection. For example, the levels of both HBsAG and HBeAG increase with robust infection. Methods of monitoring HBV antigen secretion are known in the art. In certain aspects, a robust infection is characterized by HBsAG and/or HBeAG antigen secretion of the mature hepatocytes that is about 2, 5, or 10 fold the antigen secretion of the starting population of PSC-derived hepatocytes.

Additionally, the HBV infectivity of the treated hepatocytes can be characterized by their ability to produce HBV capable of re-infecting hepatocytes. For example, mature hepatocytes can be infected with HBV and the resulting supernatant can be collected to isolate HBV produced by the mature hepatocytes. The concentrated HBV can then be used to re-infect a second culture of virus receptive hepatocytes and monitored for HBV infection.

b. Hepatocyte Maturation Markers

The cAMP and JAKi-treated hepatocytes of the present disclosure can also be characterized according to whether they express markers characteristic of hepatocyte that are in the process of maturation. Non-limiting examples of maturation markers useful in distinguishing mature hepatocytes include solute carrier family 10 (sodium/bile acid cotransporter), member 1 (SLC10A1), UDP glucuronosyltransferase 1 family, polypeptide A1 (UGT1A1), peroxisome proliferator-activated receptor gamma, coactivator 1 alpha (PPARGC1A), tyrosine aminotransferase (TAT), phosphoenolpyruvate carboxykinase 1 (PCK1), anti-apoptotic protein NR13, glutathione S-transferase alpha 2 (GSTA2), glycine-N-acyltransferase (GLYAT) and metallothionein 1M (MT1M).

Assessment of the level of expression of such markers can be determined in comparison with other cells. Positive controls for the markers of mature hepatocytes include adult primary human hepatocytes. Negative controls include the starting population of PSC-derived hepatocytes or cells of a separate lineage, such as an adult fibroblast cell line, or retinal pigment epithelial (RPE) cells.

The expression of hepatocyte markers associated with maturity can be detected at the mRNA level by Northern blot analysis, dot-blot hybridization analysis, or by real-time polymerase chain reaction (PCR) using sequence-specific primers in standard amplification methods (U.S. Pat. No. 5,843,780). Sequence data for the particular markers listed in this disclosure can be obtained from public databases, such as GenBank. Expression at the mRNA level is said to be "detectable" according to one of the assays described in this disclosure if the performance of the assay on cell samples according to standard procedures in a typical controlled experiment results in clearly discernable hybridization or amplification product within a standard time window. Unless otherwise required, expression of a particular marker is indicated if the corresponding mRNA is detectable by RT-PCR. Expression of mature hepatocyte markers as detected at the protein or mRNA level is considered positive if the level is at least 2-fold, and preferably more than 10- or 50-fold above that of a control cell, such as an iPSC-derived hepatocyte, undifferentiated pluripotent stem cell, a fibroblast, or other unrelated cell type.

III. USE OF VIRUS-RECEPTIVE HEPATOCYTES

The hepatocytes provided by methods and compositions of certain aspects of the present disclosure can be used in a variety of applications. These include, but are not limited to, transplantation or implantation of the hepatocytes in vivo; screening anti-virals, cytotoxic compounds, carcinogens, mutagens growth/regulatory factors, pharmaceutical compounds, etc., in vitro; elucidating the mechanism of liver diseases and infections; studying the mechanism by which drugs and/or growth factors operate; diagnosing and monitoring cancer in a patient; gene therapy; and the production of biologically active products, to name but a few.

A. Test Compound Screening

1. Compounds Affecting Hepatocyte Characteristics

Hepatocytes of the present disclosure can be used to screen for factors (such as solvents, small molecule drugs, peptides, and polynucleotides) or environmental conditions (such as culture conditions or manipulation) that affect the characteristics of hepatocytes provided herein.

Particular screening applications of the embodiments relate to the testing of pharmaceutical compounds in drug research. The reader is referred generally to the standard textbook In vitro *Methods in Pharmaceutical Research*, Academic Press, 1997. In certain aspects, agent-treated hepatocytes play the role of test cells for standard drug screening and toxicity assays, as have been previously performed on hepatocyte cell lines or primary hepatocytes in short-term culture. Assessment of the activity of candidate pharmaceutical compounds generally involves combining the hepatocytes provided in certain aspects of the present disclosure with the candidate compound, determining any change in the morphology, marker phenotype, or metabolic activity of the cells that is attributable to the compound (compared with untreated cells or cells treated with an inert compound), and then correlating the effect of the compound with the observed change. The screening may be done either because the compound is designed to have a pharmacological effect on liver cells, or because a compound designed to have effects elsewhere may have unintended hepatic side effects. Two or more drugs can be tested in combination (by combining with the cells either simultaneously or sequentially), to detect possible drug-drug interaction effects.

In some applications, compounds are screened initially for potential hepatotoxicity (Castell et al., 1997). Cytotoxicity can be determined in the first instance by the effect on cell viability, survival, morphology, and leakage of enzymes into the culture medium. More detailed analysis is conducted to determine whether compounds affect cell function (such as gluconeogenesis, ureogenesis, and plasma protein synthesis) without causing toxicity. Lactate dehydrogenase (LDH) is a good marker because the hepatic isoenzyme (type V) is stable in culture conditions, allowing reproducible measurements in culture supernatants after 12-24 h incubation. Leakage of enzymes such as mitochondrial glutamate oxaloacetate transaminase and glutamate pyruvate transaminase can also be used. Gomez-Lechon et al. (1996) describes a microassay for measuring glycogen, which can be used to measure the effect of pharmaceutical compounds on hepatocyte gluconeogenesis.

Other current methods to evaluate hepatotoxicity include determination of the synthesis and secretion of albumin, cholesterol, and lipoproteins; transport of conjugated bile acids and bilirubin; ureagenesis; cytochrome p450 levels and activities; glutathione levels; release of a-glutathione s-transferase; ATP, ADP, and AMP metabolism; intracellular $K+$ and $Ca2+$ concentrations; the release of nuclear matrix proteins or oligonucleosomes; and induction of apoptosis (indicated by cell rounding, condensation of chromatin, and nuclear fragmentation). DNA synthesis can be measured as [$^3$H]-thymidine or BrdU incorporation. Effects of a drug on DNA synthesis or structure can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to Vickers (1997) for further elaboration.

2. Anti-Viral Compounds

Several vaccines are available that reduce the risk of initial infection with HBV, but many individuals continue to become chronically infected with the virus. In addition, there is a large pool of existing chronic carriers—perhaps as many as 300 million worldwide—who are beyond treatment with vaccines. Development of effective methods and compositions for treatment of HBV infections is an important goal of the pharmaceutical industry. There is thus a need in the art for methods to identify new anti-HBV drugs that can be administered during and after exposure to this viral pathogen.

Accordingly, hepatocytes produced by the present methods can be used to screen for anti-viral compounds such as those useful in treating hepatitis A, B, C, and delta, Epstein-Barr virus (EBV), and cytomegalovirus (CMV). In particular embodiments, the anti-viral compound can be a compound that inhibits replication of HBV. Assessment of the activity of candidate anti-viral generally involves contacting the mature hepatocytes provided in the present disclosure with the candidate compound, determining any change in the morphology, marker phenotype, or metabolic activity of the cells that is attributable to the compound (compared with untreated cells or cells treated with an inert compound), and then correlating the effect of the compound with the observed change. For example, the change in marker phenotype for HBV can be a decrease in secretion of HBsAG and/or HBeAG antigens or a decrease in HBV cccDNA.

The screening assay is carried out using techniques that are well-known in the art including high-throughput methods. Assays are performed in the absence and presence of test compounds. Test compounds are prepared as serial three to ten-fold dilutions in solvents or buffers compatible with the assay. A test compound that decreases HBV antigen secretion by more than 30% relative to controls is a candidate for an anti-HBV agent.

Large numbers of anti-HBV test compounds could be assayed in a cost-efficient, rapid manner. Useful agents may be found within numerous chemical classes, though typically they are organic compounds, and preferably small organic compounds. Small organic compounds have a molecular weight of more than 50 yet less than about 2,500 daltons, preferably less than about 750, more preferably less than about 400 daltons. Exemplary compounds include peptides, saccharides, steroids, and the like. The compounds may be modified to enhance efficacy, stability, and pharmaceutical compatibility. Natural product extracts can also be tested, and the component that decreases HBV antigen secretion can be purified from the mixture in a subsequent step.

Test compounds for use in high-throughput screening methods may be found in large libraries of synthetic or natural substances. Numerous means are currently used for random and directed synthesis of saccharide, peptide, and nucleic acid-based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). In addition, there exist methods for generating combinatorial libraries based on peptides, oligonucleotides, and other organic compounds (Baum, C&EN, Feb. 7, 1994, page 20-26). Alternatively, libraries of natural compounds in the form of bacterial, fungal, plant and animal extracts are available from e.g. Pan Labs (Bothell, Wash.) or MycoSearch (NC), or are readily producible. Additionally, natural and synthetically produced libraries and compounds are readily modified through conventional chemical, physical, and biochemical means.

Once a test compound has been identified in vitro as a candidate anti-HBV agent, it is further tested in vitro for its ability to inhibit HBV replication and in animal model systems. Techniques that are well-known in the art may be used to enhance uptake of the compound by the cells or penetration of the compound across the cell membrane e.g. electroporation, liposome encapsulation, microinjection, or scrape loading. HBV replication is measured by monitoring the levels of intracellular and extracellular HBV DNA, using Southern blotting with radiolabelled HBV-specific probes (Sells et al., J. Virol. 62:2836, 1988). A decrease in viral DNA such as about 40% over that observed in control flasks indicates that the candidate compound is an anti-HBV agent.

Similarly, an animal model system for HBV infection comprises chimpanzees, ground and tree squirrels, Pekin ducks, or, most preferably, woodchucks. Woodchuck hepatitis virus (WHV) infection of its natural host, the eastern woodchuck, has been developed as a model of HBV-induced liver disease in humans. Chronic WHV infection can be predictably established under experimental conditions, and causes progressive liver disease (Ponsetto et al., *Hepatology* 14:16-23, 1991). Evaluation of candidate anti-HBV agents identified by the screening method described above can also be carried out in this animal model. Viremia, liver disease, and hepatocellular carcinoma are monitored in chronically infected woodchucks in the absence and presence of increasing amounts of the candidate compound. A decrease in viremia such as by about 50% to about 90% in the animal model indicates that the candidate compound is an anti-HBV agent.

Compounds identified as anti-HBV agents using the methods of the present disclosure could have different applications in the field of antiviral therapies. First, they may serve as the starting material for the design of anti-HBV agents that are more suitable than the initially identified compound for use in clinical settings. For example, once a peptide anti-HBV agent is identified, it may be systematically modified in a variety of ways to e.g. enhance its stability, solubility properties, potency, etc. Non-limiting examples of potential modifications include introducing an unnatural amino acid, such as a D-amino acid, and particularly D-alanine; and functionalizing the amino or carboxyl terminus by e.g. acylation, alkylation, esterification or amidification. Other modifications include encapsulation in e.g. liposomes, or formation of complexes with other components.

In certain aspects, it may be desirable to target a therapeutic compound to the liver. This may be achieved by any of several methods known in the art, including conjugation to an antibody that specifically recognizes liver cells; conjugation to a galactose-terminating oligosaccharide that serves as a ligand for the liver-specific asialoglycoprotein receptor; and incorporation into liposomes.

For therapeutic applications such as the treatment of HBV infection in mammals, anti-HBV agents identified by the methods of the present disclosure may be formulated with a physiologically acceptable carrier, e.g. phosphate buffered saline or deionized water. The pharmaceutical formulation may also contain excipients, including preservatives and stabilizers that are well-known in the art. Modes of administration include oral and enteral, intravenous, intramuscular, subcutaneous, transmucosal (including rectal and buccal), and by inhalation. Generally, the amount of the agent to be administered will be empirically determined, typically in the range of about 10 to 1000 pg/kg of the recipient. For peptide agents, the concentration will generally be in the range of about 100 to 500 ug/ml in the dose administered. It will be understood that the pharmaceutical formulations of the present disclosure need not in themselves contain the entire amount of the agent that is effective in treating HBV infection, as such effective amounts can be reached by administration of a single dose, or a plurality of doses of such pharmaceutical formulations.

B. Liver Therapy and Transplantation

The present disclosure also provides for the use of hepatocytes provided herein to restore a degree of liver function to a subject needing such therapy, perhaps due to an acute, chronic, or inherited impairment of liver function. Because the methods described herein increase the maturity of hepatocytes, such methods may also render such hepatocytes more receptive to transplantation and therapeutic applications.

To determine the suitability of hepatocytes provided herein for therapeutic applications, the cells can first be tested in a suitable animal model. At one level, cells are assessed for their ability to survive and maintain their phenotype in vivo. Hepatocytes provided herein are administered to immunodeficient animals (such as SCID mice, or animals rendered immunodeficient chemically or by irradiation) at a site amenable for further observation, such as under the kidney capsule, into the spleen, or into a liver lobule. Tissues are harvested after a period of a few days to several weeks or more, and assessed as to whether starting cell types such as pluripotent stem cells are still present. This can be performed by providing the administered cells with a detectable label (such as green fluorescent protein, or β-galactosidase); or by measuring a constitutive marker specific for the administered cells. Where hepatocytes provided herein are being tested in a rodent model, the presence and phenotype of the administered cells can be assessed by immunohistochemistry or ELISA using human-specific antibody, or by RT-PCR analysis using primers and hybridization conditions that cause amplification to be specific for human polynucleotide sequences. Suitable markers for assessing gene expression at the mRNA or protein level are provided in elsewhere in this disclosure. General descriptions for determining the fate of hepatocyte-like cells in animal models is provided in Grompe et al. (1999); Peeters et al. (1997); and Ohashi et al. (2000).

At another level, hepatocytes provided herein are assessed for their ability to restore liver function in an animal lacking full liver function. Braun et al. (2000) outline a model for toxin-induced liver disease in mice transgenic for the HSV-tk gene. Rhim et al. (1995) and Lieber et al. (1995) outline models for liver disease by expression of urokinase. Mignon et al. (1998) outline liver disease induced by antibody to the cell-surface marker Fas. Overturf et al. (1998) have developed a model for Hereditary Tyrosinemia Type I in mice by targeted disruption of the Fah gene. The animals can be rescued from the deficiency by providing a supply of 2-(2-nitro-4-fluoro-methyl-benzyol)-1,3-cyclohexanedione (NTBC), but they develop liver disease when NTBC is withdrawn. Acute liver disease can be modeled by 90% hepatectomy (Kobayashi et al., 2000). Acute liver disease can also be modeled by treating animals with a hepatotoxin such as galactosamine, CC14, or thioacetamide.

Chronic liver diseases, such as cirrhosis, can be modeled by treating animals with a sub-lethal dose of a hepatotoxin long enough to induce fibrosis (Rudolph et al., 2000). Assessing the ability of hepatocytes provided herein to reconstitute liver function involves administering the cells to such animals, and then determining survival over a 1 to 8 week period or more, while monitoring the animals for progress of the condition. Effects on hepatic function can be determined by evaluating markers expressed in liver tissue, cytochrome p450 activity, and blood indicators, such as alkaline phosphatase activity, bilirubin conjugation, and prothrombin time), and survival of the host. Any improvement in survival, disease progression, or maintenance of hepatic function according to any of these criteria relates to effectiveness of the therapy, and can lead to further optimization.

Hepatocytes provided in certain aspects of the present disclosure that demonstrate desirable functional characteristics according to their profile of metabolic enzymes, or efficacy in animal models, may also be suitable for direct administration to human subjects with impaired liver function. For purposes of hemostasis, the cells can be administered at any site that has adequate access to the circulation, typically within the abdominal cavity. For some metabolic and detoxification functions, it is advantageous for the cells to have access to the biliary tract. Accordingly, the cells are administered near the liver (e.g., in the treatment of chronic liver disease) or the spleen (e.g., in the treatment of fulminant hepatic failure). In one method, the cells administered into the hepatic circulation either through the hepatic artery, or through the portal vein, by infusion through an indwelling catheter. A catheter in the portal vein can be manipulated so that the cells flow principally into the spleen, or the liver, or a combination of both. In another method, the cells are administered by placing a bolus in a cavity near the target organ, typically in an excipient or matrix that will keep the bolus in place. In another method, the cells are injected directly into a lobe of the liver or the spleen.

The hepatocytes provided in certain aspects of the present disclosure can be used for therapy of any subject in need of having hepatic function restored or supplemented. Human conditions that may be appropriate for such therapy include fulminant hepatic failure due to any cause, viral hepatitis, drug-induced liver injury, cirrhosis, inherited hepatic insufficiency (such as Wilson's disease, Gilbert's syndrome, or a1-antitrypsin deficiency), hepatobiliary carcinoma, autoimmune liver disease (such as autoimmune chronic hepatitis or primary biliary cirrhosis), and any other condition that results in impaired hepatic function. For human therapy, the dose is generally between about $10^9$ and $10^{12}$ cells, and typically between about $5 \times 10^9$ and $5 \times 10^{10}$ cells, making adjustments for the body weight of the subject, nature and severity of the affliction, and the replicative capacity of the administered cells. The ultimate responsibility for determining the mode of treatment and the appropriate dose lies with the managing clinician.

C. Use in a Liver Assist Device

Certain aspects of the present disclosure include hepatocytes provided herein that are encapsulated or part of a bioartificial liver device. Various forms of encapsulation are described in *Cell Encapsulation Technology and Therapeutics*, 1999. Hepatocytes provided in certain aspects of the present disclosure can be encapsulated according to such methods for use either in vitro or in vivo.

Bioartificial organs for clinical use are designed to support an individual with impaired liver function—either as a part of long-term therapy, or to bridge the time between a fulminant hepatic failure and hepatic reconstitution or liver transplant. Bioartificial liver devices are reviewed by Macdonald et al. (1999) and exemplified in U.S. Pat. Nos. 5,290,684, 5,624,840, 5,837,234, 5,853,717, and 5,935,849. Suspension-type bioartificial livers comprise cells suspended in plate dialysers, microencapsulated in a suitable substrate, or attached to microcarrier beads coated with extracellular matrix. Alternatively, hepatocytes can be placed on a solid support in a packed bed, in a multiplate flat bed, on a microchannel screen, or surrounding hollow fiber capillaries. The device has an inlet and outlet through which the subject's blood is passed, and sometimes a separate set of ports for supplying nutrients to the cells.

Hepatocytes are prepared according to the methods described earlier, and then plated into the device on a suitable substrate, such as a matrix of MATRIGEL® or collagen. The efficacy of the device can be assessed by comparing the composition of blood in the afferent channel with that in the efferent channel—in terms of metabolites removed from the afferent flow, and newly synthesized proteins in the efferent flow.

Devices of this kind can be used to detoxify a fluid such as blood, wherein the fluid comes into contact with the hepatocytes provided in certain aspects of the present disclosure under conditions that permit the cell to remove or modify a toxin in the fluid. The detoxification will involve removing or altering at least one ligand, metabolite, or other compound (either natural or synthetic) that is usually processed by the liver. Such compounds include but are not limited to bilirubin, bile acids, urea, heme, lipoprotein, carbohydrates, transferrin, hemopexin, asialoglycoproteins, hormones like insulin and glucagon, and a variety of small molecule drugs. The device can also be used to enrich the efferent fluid with synthesized proteins such as albumin, acute phase reactants, and unloaded carrier proteins. The device can be optimized so that a variety of these functions is performed, thereby restoring as many hepatic functions as are needed. In the context of therapeutic care, the device processes blood flowing from a patient in hepatocyte failure, and then the blood is returned to the patient.

D. Distribution for Commercial, Therapeutic, And Research Purposes

For purposes of manufacture, distribution, and use, the hepatocytes of the present disclosure are typically supplied in the form of cryogenically preserved cells, a cell culture or suspension in an isotonic excipient or culture medium, optionally frozen to facilitate transportation or storage.

The present disclosure also provides different reagent systems, comprising a set or combination of cells that exist at any time during manufacture, distribution, or use. The cell sets could comprise the hepatocytes of the present disclosure and/or hepatocyte cells in a kit with reagents containing cAMP and/or JAKi for use by the end user to produce virus receptive hepatocytes of the present disclosure, perhaps also in combination with media, undifferentiated stem cells, or other differentiated cell types. The cell populations in the set sometimes share the same genome or a genetically modified form thereof. Each cell type in the set may be packaged together, or in separate containers in the same facility, or at different locations, at the same or different times, under control of the same entity or different entities sharing a business relationship.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Starting Population of iPSC-Derived Hepatocytes

The purpose of the present example was to produce hepatocytes receptive to virus infection, particularly HBV infection, for studying HBV pathogenicity in hepatocytes, particularly the process of infection and screening for anti-HBV therapeutics. A starting population of PSC-derived hepatocytes was prepared from human induced pluripotent stem cells and are sold by Cellular Dynamics International, Inc. as iCell® Hepatocytes (catalog numbers HCC-100-010-001 and PCH-100-020-001, which is a kit containing iCell® Hepatocytes 2.0 Medium Supplement).

PSC-derived hepatocytes obtained from other sources and hepatocytes made by a variety of methods (such as methods disclosed in U.S. Pat. No. 7,473,555; U.S. Pat. No. 8,283,168; U.S. Pat. No. 8,148,151; U.S. Pat. No. 7,989,204; U.S. Pat. No. 8,481,317; U.S. Patent Publication No. 20140242595; PCT/US2015/026583; all incorporated in their entirety herein by reference) may also be used as the starting hepatocyte population for this method to produce virally receptive hepatocytes, particularly to HBV infection.

Hepatitis B virus (HBV) infections cause severe disease such as acute hepatitis, chronic hepatitis, and fulminant hepatitis. HBV replicates predominantly in hepatocytes in vivo, resulting in either acute or chronic infection. The HBV particle consists of an outer lipid envelope and an icosahedral nucleocapsid core composed of protein. HBV has a surface antigen, HBsAG which is easily detected in infected cultures and patients due to its high abundance. Another HBV antigen, HBeAG, is produced during the life cycle of the virus and used to determine the outcome of treatment and analysis of chronic disease. Thus, both HBeAG and HBsAG secretion of the virus receptive hepatocytes of the present disclosure was used to determine a true infection and replication of the HBV life cycle.

The iCell® Hepatocytes (Cellular Dynamics International, Inc.) were infected with hepatitis B virus particles for about 24 hours. Next, the medium was changed and the supernatant collected every other day for about 12 days post-infection to measure the HBsAG and HBeAG secretion using ELISA kits. In the ELISA kits, monoclonal antibodies specific for HBsAg or HBeAG have been bound to the surface of each microplate well. During the course of the assay, the positive control, negative control and samples from the hepatocyte supernatant are added to the microplate wells. An enzyme-linked (horseradish peroxidase) antibody specific for HBsAg or HBeAG is added and incubated. Following a wash to remove any unbound antigen-antibody-enzyme conjugate, a TMB (3,3',5,5' tetramethylbenzidine) substrate solution is added to each well. The enzyme (HRP) and substrate are allowed to react over a 10 minute incubation period. The enzyme-substrate reaction is terminated by the addition of sulfuric acid solution. The color change is measured spectrophotometrically at a wavelength of 450±2 nm. Only those wells containing HBsAg or HBeAG and antibody-conjugate will exhibit a change in color. The intensity of this color change is proportional to the concentration of HBsAg or HBeAG in the sample.

Figure 2A:
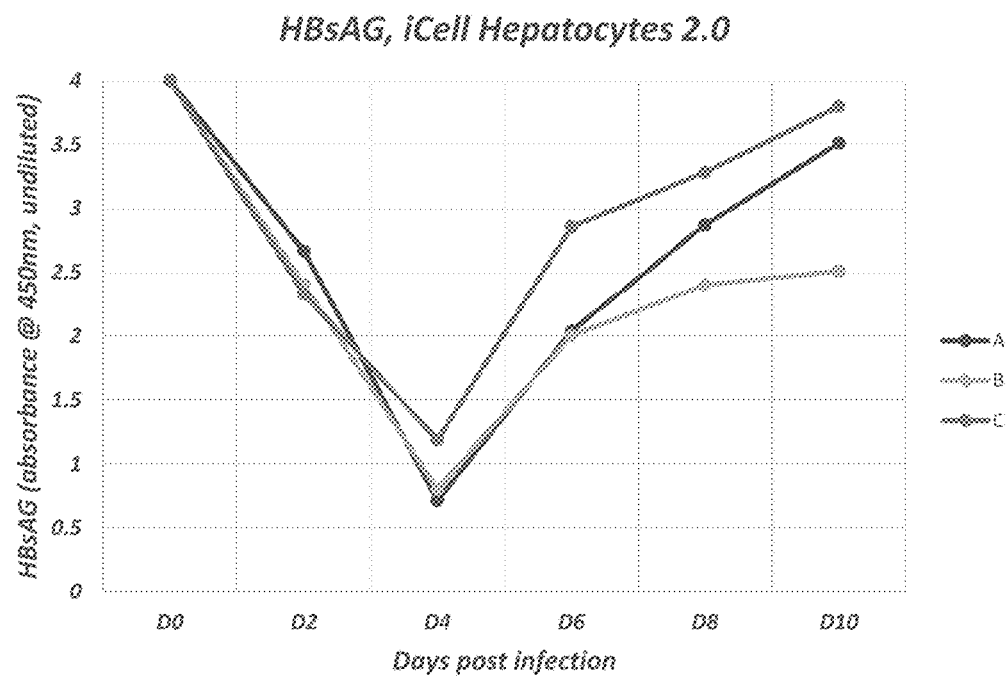
FIGS. 2A-2H: (A) iCell Hepatocytes from the different lots (A, B, C) show an increase post HBV inoculation in HBsAG present in the supernatant of infected iCell Hepatocyte cultures consistent with HBV infection but do not have detectable amounts of HBeAG. (B) Schematic showing culture conditions for producing HBV receptive hepatocytes with pre-treatment with compound A (cAMP) and compound B (Janus kinase inhibitor, JAKi). iCell Hepatocytes pre-treated with compound A (cAMP) and compound B (JAKi) and subsequently infected with HBV are positive for HBsAG (C, E) and HBeAG (D, F) in two lots of iCell Hepatocytes [lot A (E, F) and lot B (C, D)]. The highest ranges of HBsAG values are out of range of the assay at a 1:10 dilution. (C) The compound A and B culture had the highest HBsAG, followed by Compound A, Compound B, and control. (D) The compound A and B culture had the highest HBeAG, followed by Compound A, Compound B, and control. (E) The compound A and B culture had a significantly higher HBsAG as compared to control. (F) The compound A and B culture had a significantly higher HBeAG as compared to control. (G-H) Three lots of iCell Hepatocytes are receptive to HBV infection after culturing with cAMP and a JAKi as shown by the production of HBsAG (G) and HBeAG (H) after 10 days of HBV infection.

The results of the foregoing infection analysis are shown in FIG. 2A. As can be seen, the HBV-infected starting population of three different lots (A, B and C) of iCell® Hepatocytes showed an increase over time of HBsAG secretion consistent with HBV infection (FIG. 2A). However, it was found that the uninfected iCell Hepatocytes did not exhibit a detectable level of HBeAG. Thus, the foregoing assay demonstrates that iCell® Hepatocytes do not support a true HBV infection with both HBsAG and HBeAG secretion.

Example 2—Producing Virus-Receptive Hepatocytes

In this example, one example of the present disclosure is described wherein PSC-derived hepatocytes are further cultured in accordance with the present methods and then tested for HBV infectivity as in Example 1. Here, iCell® Hepatocytes were cultured in accordance with the present methods: Plating Medium was prepared comprising RPMI 1640, Oncostatin M, B27 supplement, dexamethasone, gentamycin and a hepatocyte medium supplement such as iCell® Hepatocyte 2.0 medium supplement (Table 3). A cell suspension of the iCell® Hepatocytes was diluted using room temperature Plating Medium to obtain a cell plating density of $11.2\times10^5$ cells/mL. About 100 µL of cell suspension was dispensed into each well of a collagen coated 96 well plate, resulting in $1.12\times10^5$ cells/well ($3.5\times10^5$ cells/cm$^2$). The iCell® Hepatocytes were then cultured in a cell culture incubator at 37° C. and 5% $CO_2$ for about 3-4 hours. During incubation, an aliquot of Plating Medium was equilibrated to room temperature. After incubation, the Plating Medium was aspirated from the plate using a multichannel pipette and replaced with 100 µL of room temperature Plating Medium.

TABLE 2

Material and reagents

| Material | Vendor | Catalog Number |
| --- | --- | --- |
| Polystyrene 96 well plate, conical bottom | Nunc/Fisher Scientific | 12-565-216 |
| HbsAG assay kit | Bio-Rad | 32591 |
| HbeAG assay kit | Novus Biologicals | KA0290 |
| Polyethylene glycol, 40% | Sigma | P1458-50ML |

TABLE 3

Plating Medium

| Component | Amount (mL) | Final Concentration |
| --- | --- | --- |
| RPMI | 72 | 96% |
| B27 Supplement, 50x | 1.5 | 1x |
| Oncostatin M, 10 µg/ml | 0.15 | 20 ng/ml |
| Dexamethasone, 5 mM | 0.0015 | 0.1 µM |
| Gentamicin | 0.0375 | 25 µg/ml |
| iCell® Hepatocytes 2.0 Medium Supplement | 1.5 | 1x |

To begin the induction of viral receptivity, the medium was aspirated 24 hours after plating the hepatocytes using a multichannel pipette and replaced with 100 µL of room temperature Plating Medium supplemented with cAMP at about 1 mM. The feeding of the cells was repeated every day until 5 days post plating.

Five days after plating, the medium was aspirated and replaced with Maintenance Medium RPMI B27 Supplement, Dexamethasone, Gentamicin and iCell® Hepatocytes 2.0 Medium Supplement (Table 4) supplemented with a JAK inhibitor (JAKi: EMP Millipore, Catalog No. 420099) at about 1 µM. After about 24 hours, the medium was aspirated and replaced with 100 µL of Maintenance Medium supplemented with the JAKi. The cells were cultured in the Maintenance Medium for about another day. The resultant hepatocytes were then subjected to HBV infectivity characterization and are referred to herein as "treated hepatocytes" or similar label.

TABLE 4

Maintenance Medium

| Component | Amount (mL) | Final Concentration |
| --- | --- | --- |
| RPMI | 72 | 96% |
| B27 Supplement, 50x | 1.5 | 1x |
| Dexamethasone, 5 mM | 0.0015 | 0.1 uM |
| Gentamicin | 0.0375 | 25 ug/ml |
| iCell® Hepatocytes 2.0 Medium Supplement | 1.5 | 1x |

Example 3—Hepatocyte Characterization

The treated hepatocytes from Example 2 were characterized by their receptivity to hepatitis B infection and compared to the control (untreated) iCell® Hepatocytes as described in Example 1. Both the untreated iCell® Hepatocytes and treated hepatocytes were infected with hepatitis B virus (HBV) by exposing the cells to HBV. For the HBV infection, the HB particles were mixed in Infection Medium comprising Maintenance Medium and about 4% polyethylene glycol. The hepatocyte medium was aspirated and replaced with about 100-150 µL of Infection Medium comprising 90% Maintenance Media, 4% polyethylene glycol and HBV particles. About 24 hours after the HBV infection, the medium was changed to Maintenance Medium and the supernatant was collected and stored in a separate 96 well plate for further analysis. The medium change and the supernatant collection was repeated on alternate days up to 12 days post-infection. The supernatant was stored at 4° C. for analysis.

TABLE 5

| Infection Medium | | |
|---|---|---|
| Component | Amount (mL) | Final Concentration |
| Maintenance Medium | 18 | 90% |
| Polyethylene glycol, 40% | 2 | 4% |

Figure 2B:
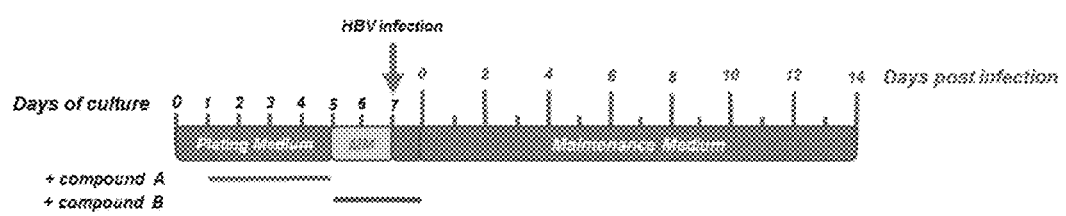
Figure 2C:
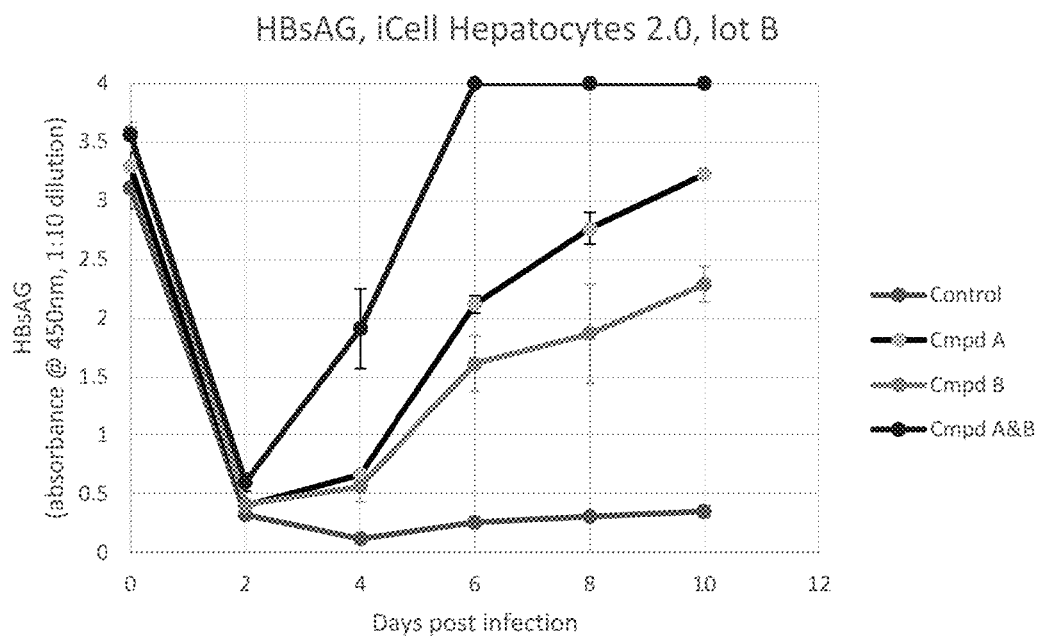
Figure 2D:
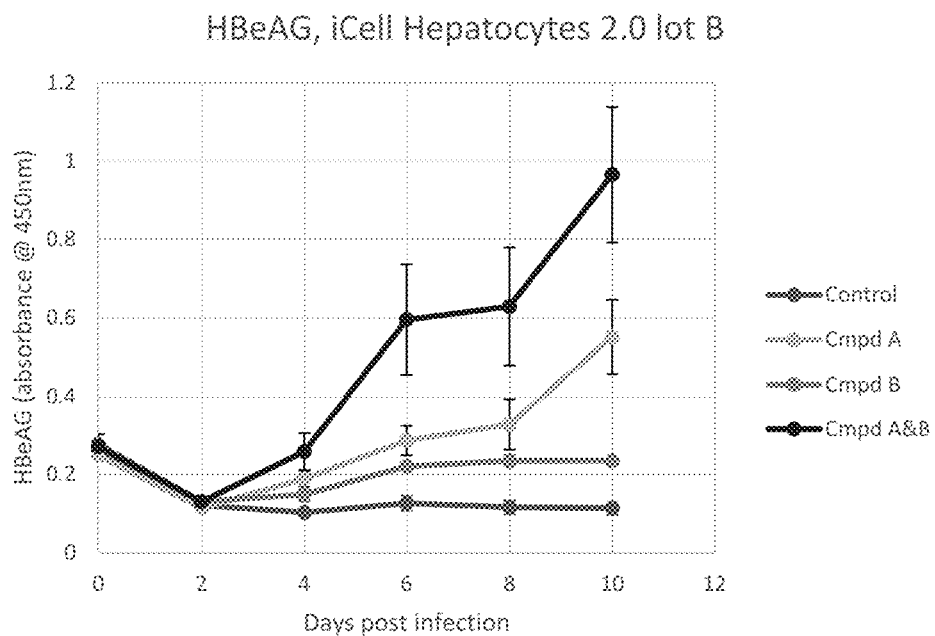
Figure 2E:
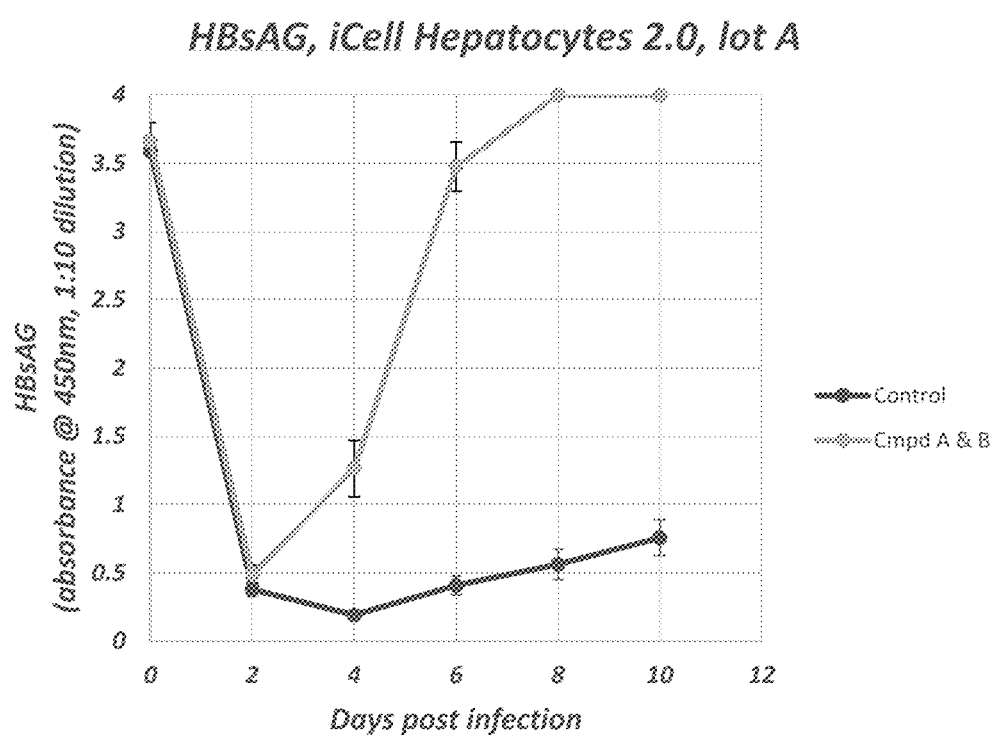
Figure 2F:
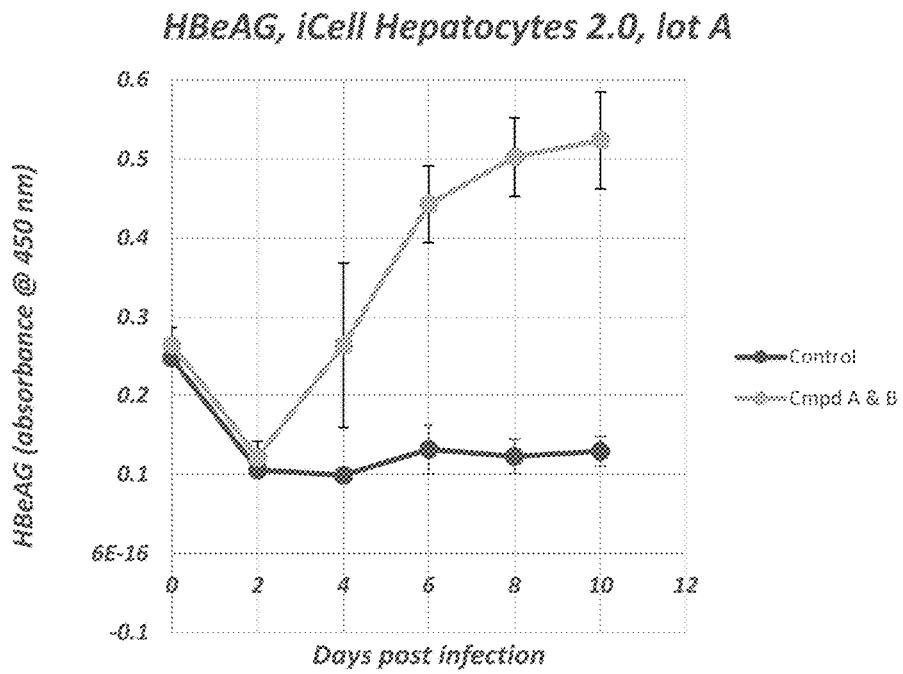
Figure 2G:
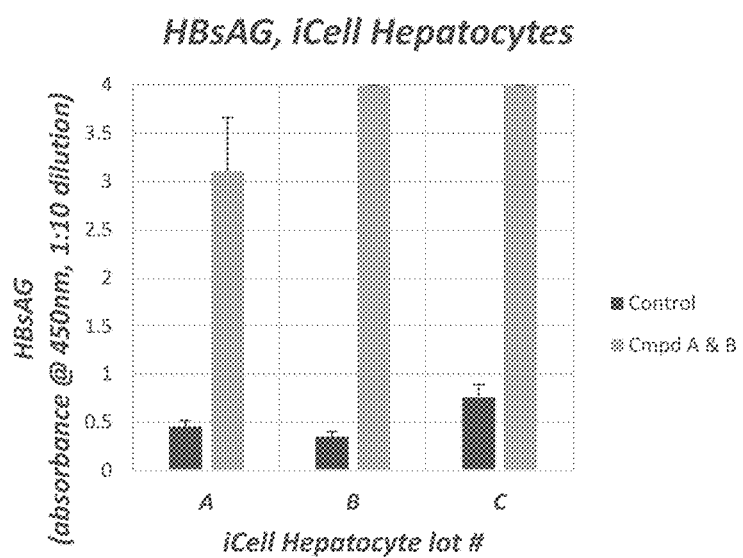
Figure 2H:
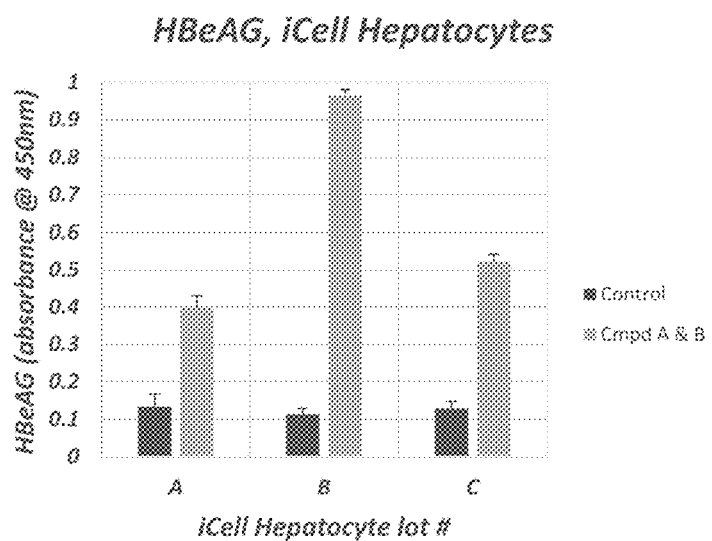

The supernatant of the HBV-infected cAMP and JAKi untreated iCell® Hepatocytes and treated hepatocytes was analyzed using the HBsAG and HBeAG ELISA kits as described above to determine receptivity to infection. Both of the antigens were used to determine whether a true infection could be realized and if replication of the HBV life cycle was evident. If the HBsAG readings fell outside of the dynamic range of the assay, the supernatant was diluted as necessary (e.g., 1:10 or higher) in Maintenance Medium before the assay was started to ensure readings within the dynamic range of the assay. A typical timeline for treating hepatocytes to induce HBV receptivity and for infection of the treated hepatocytes is depicted in FIG. 2B.

Figure 3A:
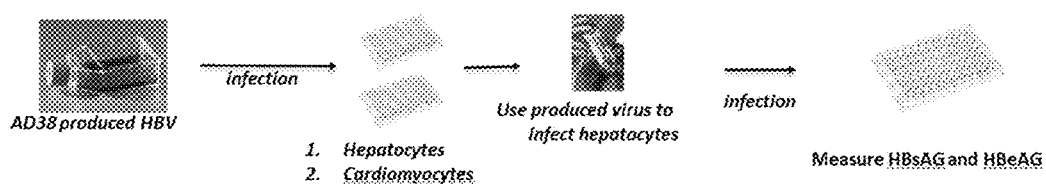
FIGS. 3A-3E: (A) Schematic showing method of assessing ability of HBV receptive hepatocytes to produce HBV capable of re-infecting hepatocytes as compared to cardiomyocytes used as a negative control. (B-C) Levels of HBsAG (B) and HBeAG (C) after primary HBV infection are shown. (D-E) Concentrated HBV from primary infection produced supernatant shows robust signs of reinfection with evidence of HBsAG (D) and HBeAG (E) in hepatocyte produced supernatant but not from cardiomyocyte produced supernatant.
Figure 3B:
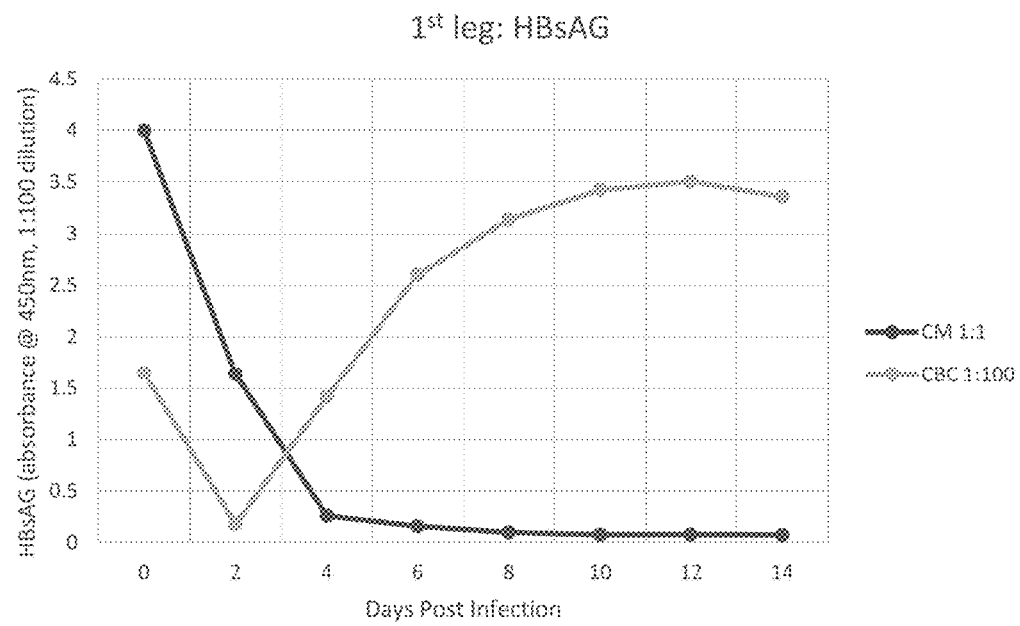
Figure 3C:
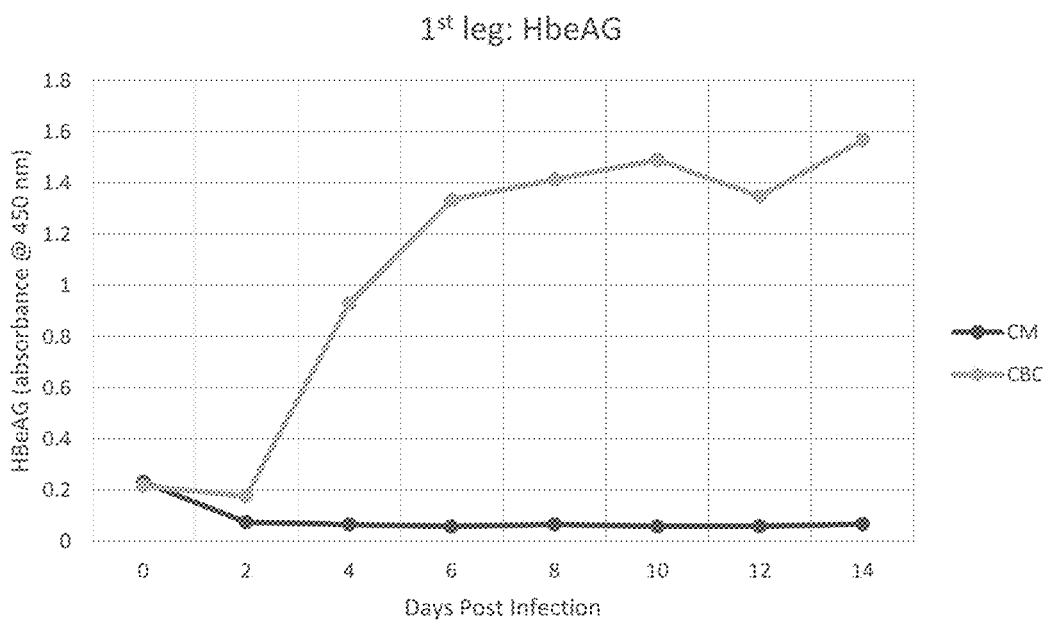
Figure 3D:
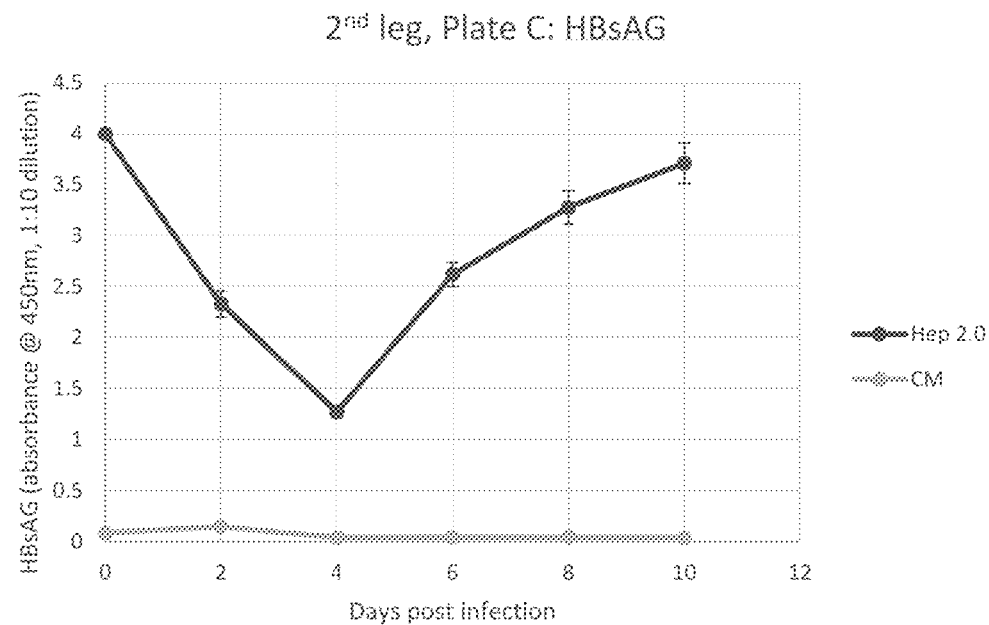
Figure 3E:
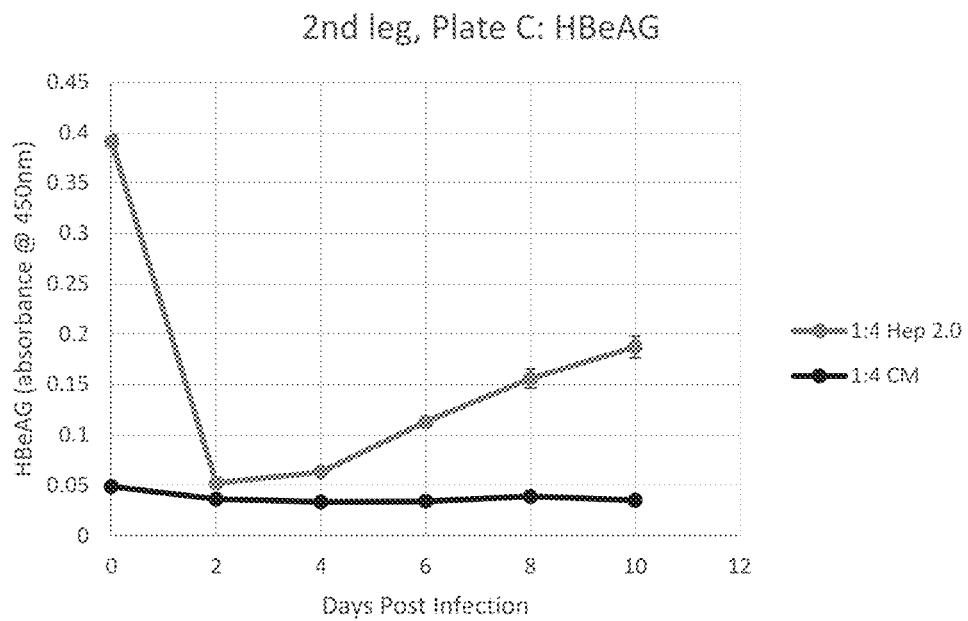

As discussed before, the iCell® Hepatocytes of Example 1 (not treated with cAMP or JAKi) did not show evidence of HBeAG. In contrast, the treated hepatocytes produced in Example 2 by treatment with cAMP and a JAK inhibitor were positive for both HBsAG and HBeAG after being infected with HBV (FIGS. 2C-2H). In particular, hepatocytes treated with cAMP and a JAK inhibitor showed a synergistic enhancement of the HBsAG and HBeAG secretion levels compared to either cAMP or a JAKi alone. Thus, the cAMP and JAKi treated hepatocytes had an enhanced ability to support hepatitis B infection as compared to the untreated iCell Hepatocytes In addition, virus produced by infected hepatocytes that had been pre-treated with cAMP and a JAKi was isolated from the supernatant and used for a secondary infection to demonstrate HBV replication and the production of fully competent virus (FIG. 3A). The treated hepatocytes of the present disclosure and cardiomyocytes as a negative control (iCell Cardiomyocytes), which are not a cell type that can support HBV infection, were infected with HBV. The HBsAG and HBeAG secretion levels were monitored for 14 days by collecting the supernatant and measuring antigen levels by ELISA kits (FIGS. 3B-3C). While the cardiomyocytes did not show any sign of infection, the treated hepatocytes showed robust signs of infection as evident from the production of HBsAG and HBeAG. Next, the HBV produced from the primary infection was concentrated from the supernatant of the treated hepatocytes and the cardiomyocytes in a secondary infection. The concentrated HBV from the cardiomyocytes exposed to HBV did not show any signs of infection (FIGS. 3D-3E), while the HBV isolated from the supernatant of the first culture of treated hepatocytes was able to robustly infect the second culture of treated hepatocytes. The ability of HBV to re-infect the hepatocytes showed evidence of the full viral life cycle in the treated hepatocyte culture.

Figure 4A:
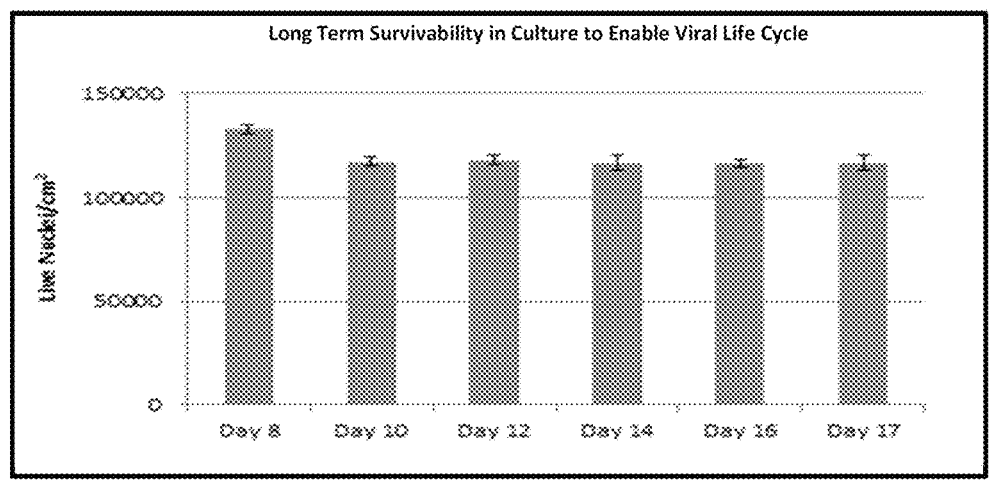
FIGS. 4A-4B: (A) Long term survivability of PSC-derived hepatocytes cultured in the presence of cAMP and JAKi is shown. (B) The expression of the HBV receptor NTCP is shown by the expression of the SLC10A1 gene.
Figure 4B:
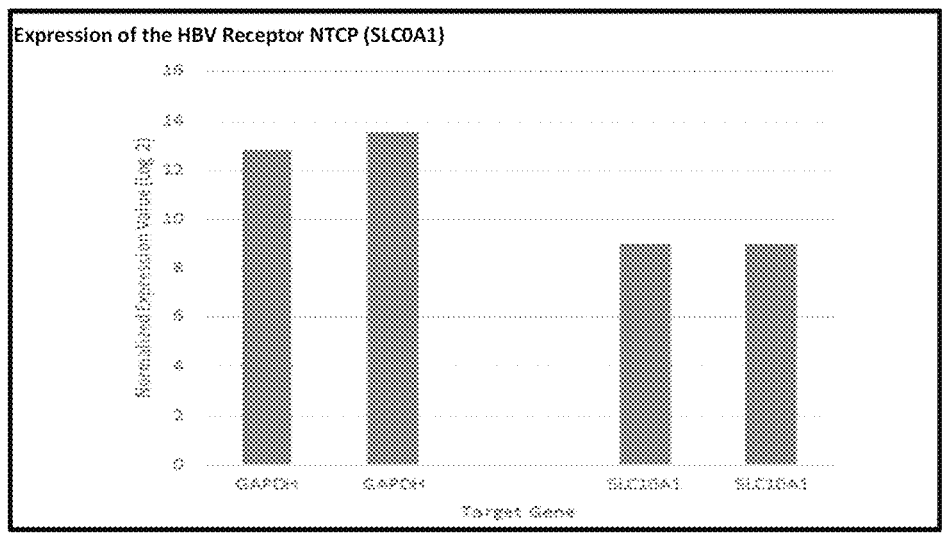

The treated hepatocytes were also found to have long-term viability in culture (FIG. 4A) and increased expression of the HBV receptor NTCP (FIG. 4B). Thus, the treated hepatocytes produced in Example 2 were characterized to have reached the required level of maturity so as to be receptive to and supportive of HBV infection.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aman and Leonard, Current Biology, 7:R784-788, 1997.
Amit et al., Dev. Bio., 227:271-278, 2000.
Chen et al., Hepatology, 55(44): 1193-203, 2012.
Chung et al. Science, 278: 1803-1805, 1997.
Gazit et al. J. Med. Chem., 32: 2344-2352, 1989.
Gripon et al., J. Virol, 62(11)4136-4143, 1988.
Gripon et al., Virology, 192(2)534-540, 1993.
Guillouzo et al., Environ Health Perspect, 106: 511-532, 1998.
Mann et al., Genetic Engineering and Biotechnology News: Assay Tutorials, 33: 9, 2013.
Nassal et al., M Virus Research, 134: 235-249, 2008.
Nicholson and Hilton J. Leukocyte Biol., 63: 665-668, 1998.
Ohya et al. J. Biol. Chem., 272: 27178-27182, 1997.
PCT Publication No. WO 2007/069666
Published U.S. Patent Application No. 2009/0246875
Published U.S. Patent Application No. 2010/0210014
Published U.S. Patent Application No. 2012/0276636
Reubinoff et al., Nat. Biotechnol., 18:399-404, 2000.
Smith, In: Origins and Properties of Mouse Embryonic Stem Cells, Annu. Rev. Cell. Dev. Biol., 2000.
Takahashi et al., Cell, 126:663-676, 2007.
Thomson and Marshall, Curr. Top. Dev. Biol., 38:133-165, 1998.
Thomson and Odorico, J. Trends. Biotechnol., 18:53-57, 2000.
Thomson et al., Science, 282:1145, 1998.
U.S. Pat. No. 5,843,780
U.S. Pat. No. 5,843,780
U.S. Pat. No. 6,103,470
U.S. Pat. No. 6,200,806
U.S. Pat. No. 6,416,998
U.S. Pat. No. 7,029,913
U.S. Pat. No. 7,442,548
U.S. Pat. No. 7,442,548
U.S. Pat. No. 7,598,364
U.S. Pat. No. 7,989,425
U.S. Pat. No. 8,058,065
U.S. Pat. No. 8,071,369
U.S. Pat. No. 8,129,187
U.S. Pat. No. 8,268,620
U.S. Pat. No. 8,278,620
U.S. Pat. No. 8,741,648
U.S. Pat. No. 8,900,871
U.S. Patent Publication No. 2003/0211603
U.S. Patent Publication No. 2003/0211603
U.S. Patent Publication No. 2014/0242595

Wang et al. *J. Immunol.*, 162(7): 3897-3904, 1999.
Xu et al., *Nat. Biotechnol.*, 19:971-974, 2001.
Ying et al., *Cell*, 115:281-292, 2003.
Yoshimura et al. *EMBO J.*, 14: 2816-2826, 1995.

What is claimed is:

1. An in vitro method of producing virus-receptive pluripotent stem cell-derived hepatocytes comprising:
   (a) obtaining pluripotent stem cell (PSC)-derived hepatocytes; and
   (b) culturing the PSC-derived hepatocytes in media comprising cyclic adenosine monophosphate (cAMP) and a Janus kinase inhibitor (JAKi), thereby producing virus receptive hepatocytes.

2. The method of claim 1, wherein the cAMP and JAKi are cultured sequentially in different media.

3. The method of claim 2, wherein the cAMP is administered in a first medium and the JAKi is administered in a second medium.

4. The method of claim 1, wherein the pluripotent stem cell is human.

5. The method of claim 1, wherein the pluripotent stem cell is an embryonic stem cell.

6. The method of claim 1, wherein the pluripotent stem cell is an induced pluripotent stem cell.

7. The method of claim 1, wherein the JAKi is 2-(1,1-Dimethylethyl)-9-fluoro-3,6-dihydro-7H-benz[h]-imidaz[4,5-f]isoquinolin-7-one (JAK Inhibitor 1), 1,2,3,4,5,6-Hexabromocyclohexane, or (E)-4,4'-(1,2-Diethyl-1,2-ethenediyl)bis[2-[(diethylamino)methyl]-phenol (9CI), 4,4'-(3E)-Hex-3-ene-3,4-diylbis{2-[(diethylamino)methyl]phenol} (NSC33994).

8. The method of claim 1, wherein the JAKi is present at a concentration of about 0.1 µM to about 5 µM.

9. The method of claim 8, wherein the JAKi is present at a concentration of about 1 µM.

10. The method of claim 1, wherein the cAMP is present at a concentration of about 0.1 mM to about 3 mM.

11. The method of claim 10, wherein the cAMP is present at a concentration of about 1 mM.

12. The method of claim 1, wherein the virus receptive hepatocytes have an increased expression of at least one hepatocyte maturation or viral infectivity gene relative to expression in the PSC-derived hepatocytes.

13. The method of claim 12, wherein the hepatocyte maturation or viral infectivity gene is selected from the group consisting of UGT1A1, PPARGC1A, TAT, PCK1, NR13, SLC10A1, GSTA2, GLYAT and MT1M.

14. The method of claim 1, wherein cAMP is present in the medium from about 2 days to about 6 days.

15. The method of claim 1, wherein the JAKi is present in the medium from about 1 day to about 3 days.

16. The method of claim 1, wherein the media is serum-free or defined media.

17. The method of claim 1, wherein the virus receptive hepatocytes have an enhanced ability to support a hepatitis B virus (HBV) infection and/or a hepatitis C virus (HCV) infection relative to the PSC-derived hepatocytes.

18. The method of claim 1, further comprising infecting the virus receptive hepatocytes with hepatitis B virus.

19. The method of claim 18, wherein the virus receptive hepatocytes have an increase in secretion of at least one HBV surface antigen.

20. The method of claim 19, wherein the at least one HBV surface antigen is HBsAG or HBeAG.

21. The method of claim 20, wherein the increase in surface antigen secretion is at least 2 fold relative to PSC-derived hepatocytes infected by HBV.

22. The method of claim 20, wherein the increase in surface antigen secretion is at least 5 fold relative to PSC-derived hepatocytes infected by HBV.

23. The method of claim 20, wherein the increase in surface antigen secretion is at least 10 fold relative to PSC-derived hepatocytes infected by HBV.

24. The method of claim 18, wherein the virus receptive hepatocytes produce hepatitis B virus capable of infecting other virus receptive hepatocytes.

* * * * *